United States Patent [19]

Vollmann

[11] Patent Number: 4,467,810
[45] Date of Patent: Aug. 28, 1984

[54] MULTI-MODE MICROPROCESSOR-BASED PROGRAMMABLE CARDIAC PACER

[75] Inventor: William Vollmann, Miami Lakes, Fla.

[73] Assignee: Cordis Corporation, Miami, Fla.

[21] Appl. No.: 430,507

[22] Filed: Sep. 30, 1982

[51] Int. Cl.³ .............................................. A61N 1/36
[52] U.S. Cl. ............................................ 128/419 PG
[58] Field of Search ................................ 128/419 PG

[56] References Cited

U.S. PATENT DOCUMENTS

| | | | |
|---|---|---|---|
| 4,208,008 | 6/1980 | Smith | 128/419 PG |
| 4,222,385 | 9/1980 | Backhouse | 128/419 PG |
| 4,313,441 | 2/1982 | Buffet | 128/419 PG |
| 4,390,021 | 6/1983 | Spurrell et al. | 128/419 PG |
| 4,418,695 | 12/1983 | Buffet | 128/419 PG |
| 4,424,812 | 1/1984 | Lesnick | 128/419 PG |

FOREIGN PATENT DOCUMENTS

| | | | |
|---|---|---|---|
| 2494119 | 5/1982 | France | 128/419 PG |
| 2026870 | 2/1980 | United Kingdom | 128/419 PG |

*Primary Examiner*—William E. Kamm
*Attorney, Agent, or Firm*—Kenway & Jenney

[57] ABSTRACT

An instruction memory for a microprocessor based cardiac pacer is equipped with code means defining improved pacing routines for accomplishing a programmably selectable 2:1 block mode in which every other atrial sense output is automatically ignored above a programmed maximum atrial rate. The 2:1 block option is preselected via the initialization routine. The atrial refractory period becomes programmable by equating it with the programmed maximum rate interval. As an alternative to 2:1 block mode, the pacer also offers VVI fallback pacing routine which can be automatically substituted for the main pacing routine. While atrial tachycardia continues to be monitored during the fallback routine, the criteria for resuming normal pacing are made different from the criteria for entering the fallback routine. In addition, before exiting the fallback routine, the R-R interval is lengthened by an amount to shift the phase of R-waves relative to P-waves. Both refractory periods and the real time clock register are adjusted by the main pacing routine to account for blanking. After any programming, normal operation is resumed by re-entering the main pacing routine as if it were at the end of a ventricular event.

13 Claims, 17 Drawing Figures

FIG. 9

```
RECORD NUMBER 0001
            71 20 90 82   A2 A6 86 F4   A6 12 92 FB
04 3A 06 86  CE 7B 00 F8   6E BD F8 5F   AD F8 44 BF
F8 40 AF F8  48 BE F8 48   AE F8 15 BA   F8 18 89 90
B2 B4 A3 BC  F3 10 B7 F8   8F A1 F8 02   B1 F8 C9 A8
68 D1 55 46  3C 35 2B 21   1B 19 4D 41   38 32 C6 09
0C 12 6E 53  59 5F 65 7B   7A D4 04 30   6A 7B D4 7A
D4 30 6A 7B  D4 D4 7A 30   6A 7B D4 D4   D4 7A D4 D4
30 82 F8 00  A3 A8 1B 99   A9 29 96 3A   3A 35 8C F3
RECORD NUMBER 0002
            07 A0 F8 08   30 84 D0 4C   FF 01 3A 84
30 82 30 7B  F3 3B A0 30   82 99 83 CD   D3 D9 E6 EA
F4 3A 9F 64  65 30 AD FF   01 3A A7 64   6D 30 AD FF
01 3A 81 6C  65 F3 C0 B7   D1 B7 01 3A   B9 66 67 30
C7 FF 01 3A  C1 66 6F 30   C7 FF 01 3A   CB 6E 67 F8
00 36 D1 B6  D1 FC 4E A2   02 BD D1 FC   4F A2 02 A2
D1 FC 42 8F  9C 3A E5 9F   A2 F0 FF 03   B9 D1 FC 35
AF D1 FC 46  37 E3 BE F3   15 B9 3C D1   FC 4A AE C1
RECORD NUMBER 0003
            D1 41 FF 01   3A FA 30 F8   04 01 F8 01
A8 99 A9 1B  3A 3A 34 96   3A 39 35 3B   8E A2 83 F7
32 6A 97 3A  66 89 32 21   29 D4 04 30   07 90 3C 83
9F A2 88 F5  3B 00 13 13   83 FF C6 33   90 0C 30 C2
D4 01 2A 30  16 30 10 8E   A2 93 F7 33   47 99 F7 A9
F0 30 48 38  C4 C4 88 FC   0D A8 89 FF   00 33 62 F8
00 A9 9A FF  0D AA D4 BA   93 32 64 23   30 07 30 55
30 60 C4 C4  30 83 69 8D   A4 D4 39 FF   0C 33 96 F9
RECORD NUMBER 0004
            00 A9 88 FC   0C A8 94 FF   0C AA D4 A6
D0 30 5C 8F  A2 38 F7 33   8D D4 01 20   07 61 90 A4
D4 F8 04 A8  D4 32 99 FF   04 30 06 30   75 9C C2 C3
76 CC 03 00  FF FF FF FF   FF FF FF FF   FF FF FF FF
FF FF FF FF  FF FF FF FF   FF FF FF FF   FF FF FF FF
FF FF FF FF  FF FF FF FF   FF FF FF FF   FF FF FF FF
FF FF FF FF  FF FF FF FF   FF FF FF FF   FF FF FF FF
FF FF FF FF  FF FF FF FF   FF FF FF FF   FF FF FF FF
RECORD NUMBER 0005
            FF FF FF FF   FF FF FF FF   FF FF FF FF
FF FF FF FF  1B D4 05 6F   A2 88 F5 30   23 D0 9F A2
89 F7 3B 1F  97 3A 21 3C   0C F8 65 A4   D4 D4 2F C0
F8 05 A8 D0  C0 30 0C D4   02 30 15 90   32 38 F3 02
32 87 90 F8  03 3A 38 13   F8 66 30 3D   F8 03 20 F9
6F A0 F8 00  AB AA A8 F8   08 A9 F8 23   44 E1 70 20
7A 1B 3E 5E  3E 5E 3E 5E   3E 5E 3E 5E   3E 5E 3E 5E
30 A5 36 4D  36 4D 36 4D   36 4D 36 4D   36 4D 36 4D
RECORD NUMBER 0006
            86 FF C8 3B   27 A8 FF 20   33 8F 32 95
FF 01 32 83  F8 00 80 F8   13 30 3D 87   69 0C 65 69
F8 02 BD F8  00 30 3D 88   FA 07 FC 91   A4 04 A4 88
F6 F6 F6 D4  30 27 BC F3   DF A4 04 30   F9 F8 F9 A4
3E E9 1B 8A  32 E3 2A 8E   A2 38 F7 32   D9 C4 C4 8F
A2 88 F7 33  DF F8 00 A8   D1 D1 81 D1   D1 7B D1 D1
D1 7A 88 32  D0 D4 03 D1   D4 34 D1 68   FC D4 A3 30
A8 8A 3A E5  69 30 C5 D4   03 30 A8 30   AF D1 D1 30
RECORD NUMBER 0007
            DF F8 00 A3   90 F8 02 32   87 30 38 FF
FF FF FF FF  FF FF FF FF   FF FF FF FF   F8 0C AA A8
A5 9F A2 02  FC 04 A7 B5   1B 27 9E A2   95 F7 33 36
15 97 3A 38  3C 39 9F A2   89 F5 F8 00   A8 D0 38 30
F3 06 A3 8A  3A 40 96 3A   45 35 65 87   32 47 C4 C4
30 0C 3C 15  D0 D4 01 30   27 D0 30 27   2A D4 01 30
34 30 2F 69  9A FF 0D AA   89 FC 0D A8   8D A4 D4 D4
AD D0 83 FB  02 3A 60 95   FC 04 30 67   95 FF C0 30
RECORD NUMBER 0008
            67 1A 95 A7   83 32 6C 23   30 0C A9 85
A2 F0 A8 C0  01 07 A3 CC   01 07 FF FF   FF FF FF FF
FF FF FF FF  FF FF FF FF   FF FF FF FF   FF FF FF FF
FF FF FF FF  FF FF FF FF   FF FF FF FF   FF FF FF FF
FF FF FF FF  FF FF FF FF   FF FF FF FF   FF FF FF FF
FF FF FF FF  FF FF FF FF   FF FF FF FF   FF FF FF FF
FF FF FF FF  FF FF FF FF   FF FF FF FF   FF FF FF FF
FF FF FF FF  FF FF FF FF   FF FF FF FF   FF FF FF FF
RECORD NUMBER 0009
            FF FF FF FF   FF FF FF FF   FF FF FF FF
FF FF FF FF  FF FF FF FF   FF FF FF FF   FF FF FF FF
FF FF FF FF
```

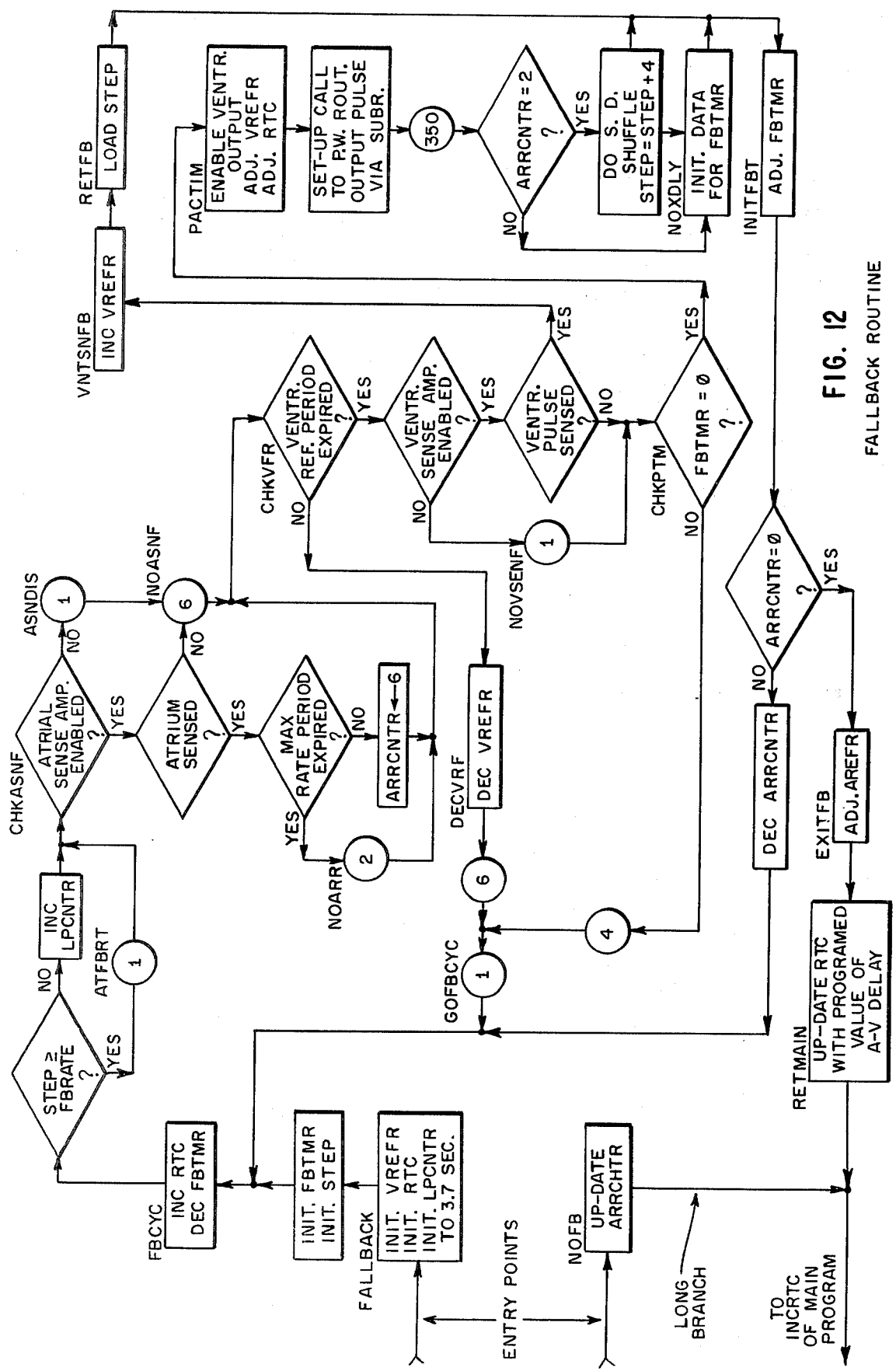
FIG. 12 FALLBACK ROUTINE

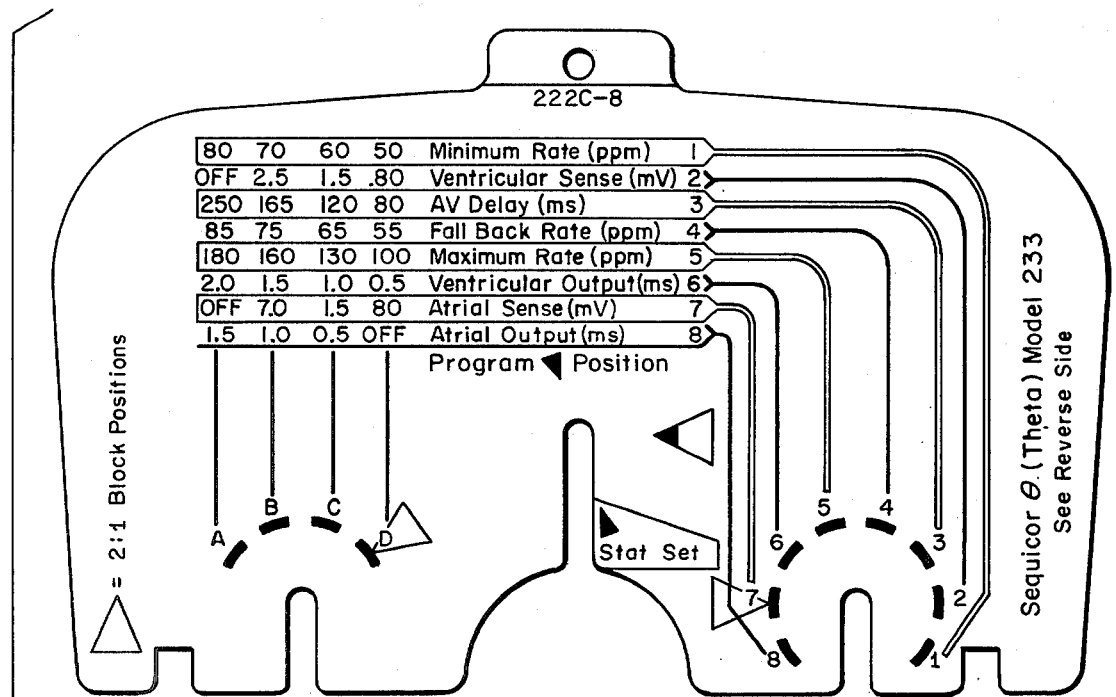
FIG. 14
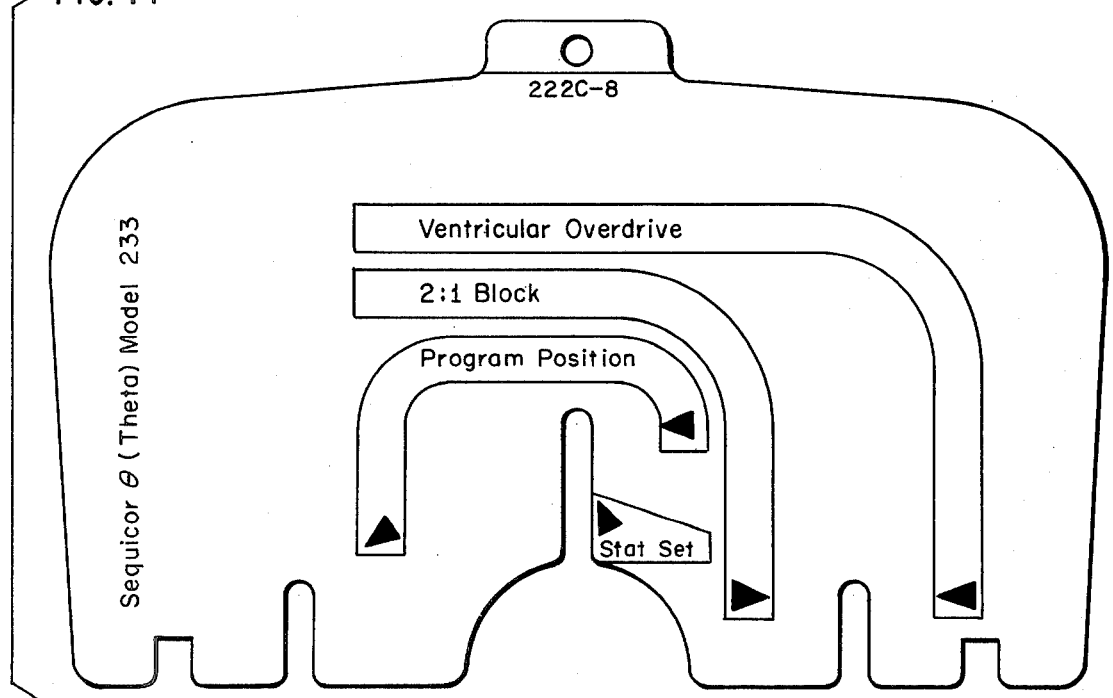

OVERDRIVE ROUTINE

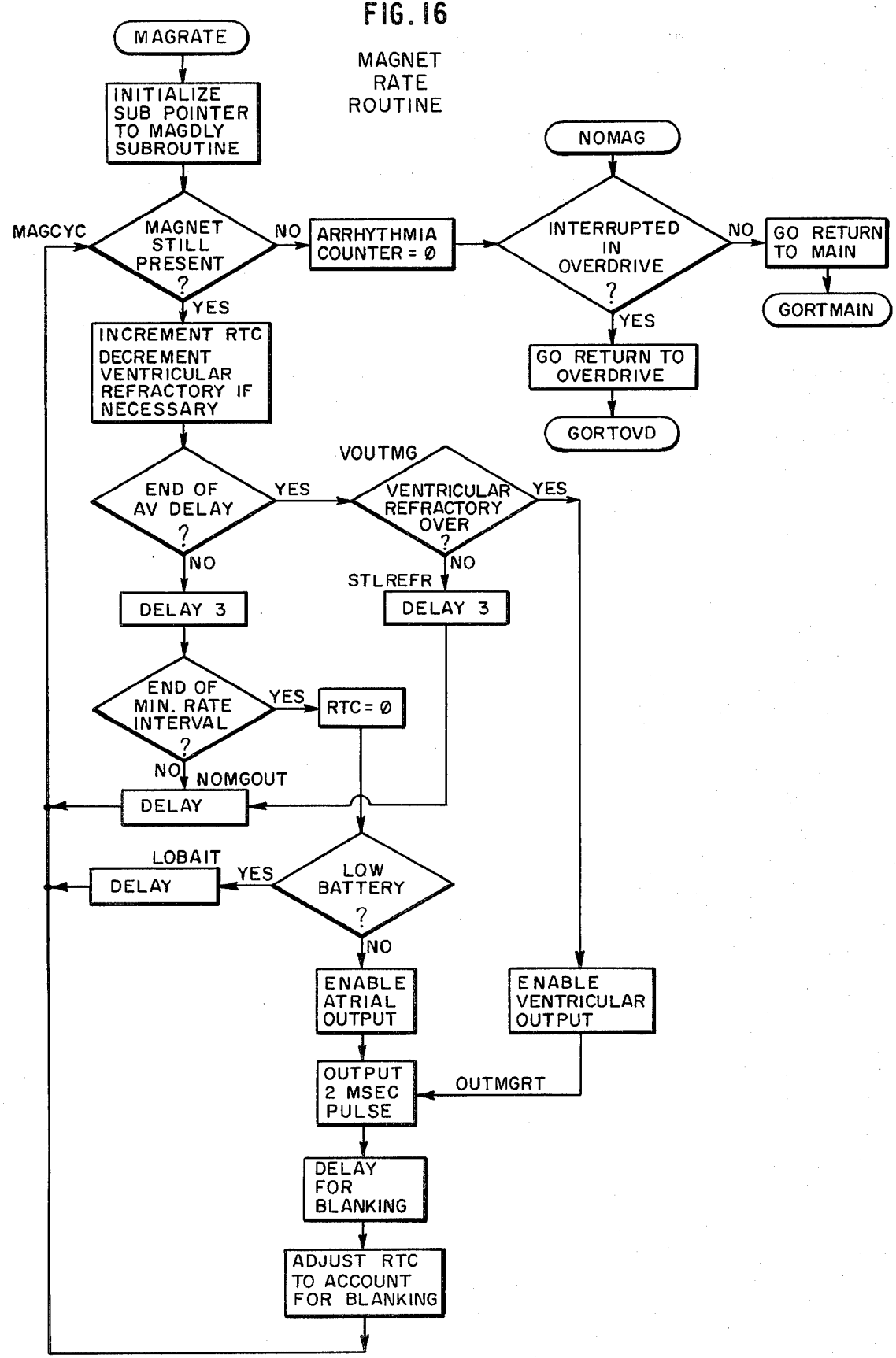

MULTI-MODE MICROPROCESSOR-BASED PROGRAMMABLE CARDIAC PACER

CROSS REFERENCE TO RELATED APPLICATION

The subject matter of this application is closely related to the subject matter of U.S. Patent application Ser. No. 207,003 entitled, "Multi-Mode Microprocessor-Based Programmable Cardiac Pacer" filed Nov. 14, 1980 by Leckrone et al., (hereinafter referred to as the 207,003 application), assigned to the assignee of the present application and incorporated herein by reference in its entirety.

BACKGROUND OF THE INVENTION

The invention relates generally to cardiac pacers, and more particularly to noninvasively programmable implantable cardiac pacers employing microcomputer techniques.

The two major pumping chambers in the heart are the left and right ventricles. Simultaneously contracting, these chambers expel blood into the aorta and the pulmonary artery. Blood enters the ventricles from the left and right atria, respectively. The atria are smaller antechambers which contract in a separate action which precedes the major ventricular contraction by an interval of about 100 milliseconds (ms), known as the AV delay, approximately one-eighth of the cardiac cycle. The contractions arise from a wave of electrical excitation which begins in the right atrium and spreads to the left atrium. The excitation then enters the atrio-ventricular (AV) node which delays its passage via the bundle of His into the ventricles.

Electrical signals corresponding to the contractions appear in the electrocardiogram. A small signal known as the P-wave accompanies atrial contraction while a much larger signal, known as the QRS complex, with a predominant R-wave, signifies ventricular contraction. Ventricular repolarization prior to the next contraction is marked by a small signal in the electrocardiogram known as the T-wave.

The physiology of the heart is known to be compatible with various interactive pacing systems. The P and R waves can be very reliably detected as timing signals by electrical leads in contact with the respective heart chambers and used to synchronize and inhibit stimulation pulses with natural cardiac activity. The typical implanted cardiac pacer operates by supplying missing stimulation pulses on a pacing lead attached to the ventricle. The R-wave can be sensed by the same lead. An additional lead contacts the atrium to sense P-waves, if desired. In AV sequential pacers, discussed below, the atrial lead is also used for atrial stimulation.

One of the problems treated by cardiac pacers is heart block caused by impairment of the ability of the bundle of His to conduct normal excitation from the atrium to the ventricle. It has long been apparent that in treating this form of heart disease it is desirable to base stimulation of the ventricles on the P-wave cycle. This synchronization maintains the heart's normal physiological pacing pattern. Thus, the sino-atrial node, which governs the interval between atrial depolarizations (i.e., the atrial rate) according to the body's needs, controls the artificial ventricular rate in the normal manner.

Patients without normal atrial activity, as in symptomatic bradycardia, often have a need for atrial stimulation as well as ventricular stimulation which alone achieves about seventy-five percent of the combined volume flow. AV sequential pacers have been proposed for stimulating the atria and the ventricles. The system in the 207,003 application, for example, senses and stimulates on both atrial and ventricular leads to provide atrial-based, AV sequential, ventricular-inhibited pacing also referred to as dual demand pacing (DDD).

In the past, pacers offered to the medical community have been implemented by analog or digital timing techniques. Digitally timed pacers with externally programmable pulse parameters have been on the market for several years. For example, the "Omni-Atricor" marketed by the assignee of the present applicaiton, Cordis Corporation, employs a reed switch in the implanted pacer which responds to a pulsating magnetic field produced by a magnetic impulse programmer such as Cordis' programmer 222B to program rate, pulse amplitude and other variables. The reed switch is also used to activate a magnet rate mode when a permanent magnet is placed near the pacer causing it to revert to a fixed rate mode in which it will not respond to natural activity.

Cardiac pacers are life supporting, therapeutic medical devices. They are surgically implanted and remain within a living person's body for years. The vital considerations in cardiac pacing technology tend to dictate a conservative approach, if not reluctance, toward commercially exploiting new developments in electronic circuitry. These tendencies are enhanced by the fact that the relatively simple functional requirements of prior art pacers have been easily implemented using preexisting well-established hardware circuit configurations, and also by the state of the art in compact batteries. The nonrechargeable lithium compound batteries used in most pacers today limit current drain to avoid unnecessary replacements which require surgery and reprogramming of an expensive new pacer. Reliability is the chief concern, however, followed closely by compactness and low current drain.

Digital microcomputers have been suggested for implants before. See, for example, the 207,003 application and U.S. Patent Application Ser. No. 195,665, filed Oct. 9, 1980 by Alan Lesnick, entitled "Implantable Externally Programmable Microprocessor-Controlled tissue Stimulator", assigned to the assignee of the present application. Microcomputers are suited by design to making simple or complex logical decisions and taking alternative action repeatedly in the same manner. Microprocessor technology presents the challenge of making a pacing routine which monitors sense amplifier outputs indicative of spontaneous activity of the heart and safely determines and provides the type of stimulation that would be best suited to the existing condition. It is conceivable that the pacer of tomorrow will diagnose the patient's cardiac function, and prescribe and select the correct stimulation routine for treatment or pacing. The chief problem in exploiting this technology is safety despite increased opportunities for versatility and complexity.

Many patients who need cardiac pacers have a history of cardiac arrhythmia. One of the most feared arrhythmias, particularly for patients wearing physiological pacers, is atrial tachycardia. In this disorder the sinus rate accelerates uncontrollably. Heart rates of 180 to 300 beats per minute are typical. The problem with atrial tachycardia is how to define it electrically so that the implanted microprocessor will be able to recognize it, how to react to it when it happens, how to decide when it is over, and how to safely resume normal pacing.

The atrial arrhythmia response mode disclosed in the 207,003 application embodies some of the key elements of a practical atrial tachycardia response system. Since it is designed to choose and execute a complex treatment automatically, there is ample interest in safeguards designed to assure even greater control of the entry and exit modes for this novel response system.

Ideally, in a microprocessor-based pacer it is desirable to retain the programmability of pacer parameters and to enable the use of preexisting programmers which have already been widely marketed. Programming, however, at least in the approach taken in the 207,003 application, interrupts the pacing routine asynchronously at a random point. The manner of returning to the main pacing routine after such programming is another one of the subjects of the present invention.

SUMMARY OF THE INVENTION

An instruction memory for a microprocessor based cardiac pacer is equipped with code means defining improved pacing routines for accomplishing a programmably selectable 2:1 block mode in which every other atrial contraction is automatically ignored above a programmed maximum atrial rate. The 2:1 block option is automatically preselected when a standard set of pacing parameters is selected via the initialization routine. The atrial refractory period becomes programmable by virtue of its equation with the programmable maximum rate interval, unlike the ventricular refractory period, for example, which remains fixed.

As a programmable alternative to 2:1 block mode, the pacer also offers an initially faster decreasing rate VVI fallback pacing routine which can be automatically substituted for the main pacing routine when predetermined atrial tachycardia detection criteria are met. During execution of the fallback routine, atrial tachycardia continues to be monitored. However, the criteria for exiting the fallback routine and resuming normal pacing are made different from the criteria for entering the fallback routine. In addition, before exiting the fallback routine, the R—R interval for VVI pacing is lengthened by an amount to shift the phase of the R-waves relative to P-waves so that none remain hidden by blanking.

In the preferred embodiment atrial tachycardias are never sensed during the atrial refractory period. In the fallback mode as in the main pacing routine, the atrial and ventricular refractory periods are nominally fixed. However, both refractory periods and the real time clock register are automatically adjusted by the main pacing routine to account for blanking. The improved main pacing routine also includes means for blanking the atrial sense amplifier upon ventricular sensing as well as stimulation.

After a programming interrupt is serviced by the pacer, normal operation is resumed by re-entering the main pacing routine as if it were at the end of a ventricular event to give the pacer time to resynchronize with intrinsic cardiac activity.

BRIEF DESCRIPTION OF THE DRAWINGS

FIG. 9 is a bit pattern profile or table of contents for the read only memory (ROM) of FIG. 1 at consecutive memory locations in hexadecimal digits.

FIG. 12 is a flow chart of the fallback pacing routine.

FIG. 14 shows plan views of the front and back of the program card for use with an existing Cordis Corporation Model 222 or 222B programmer to program the pacer of FIG. 1.

FIG. 16 is a flow chart of the magnet rate routine.

Figure 9A:
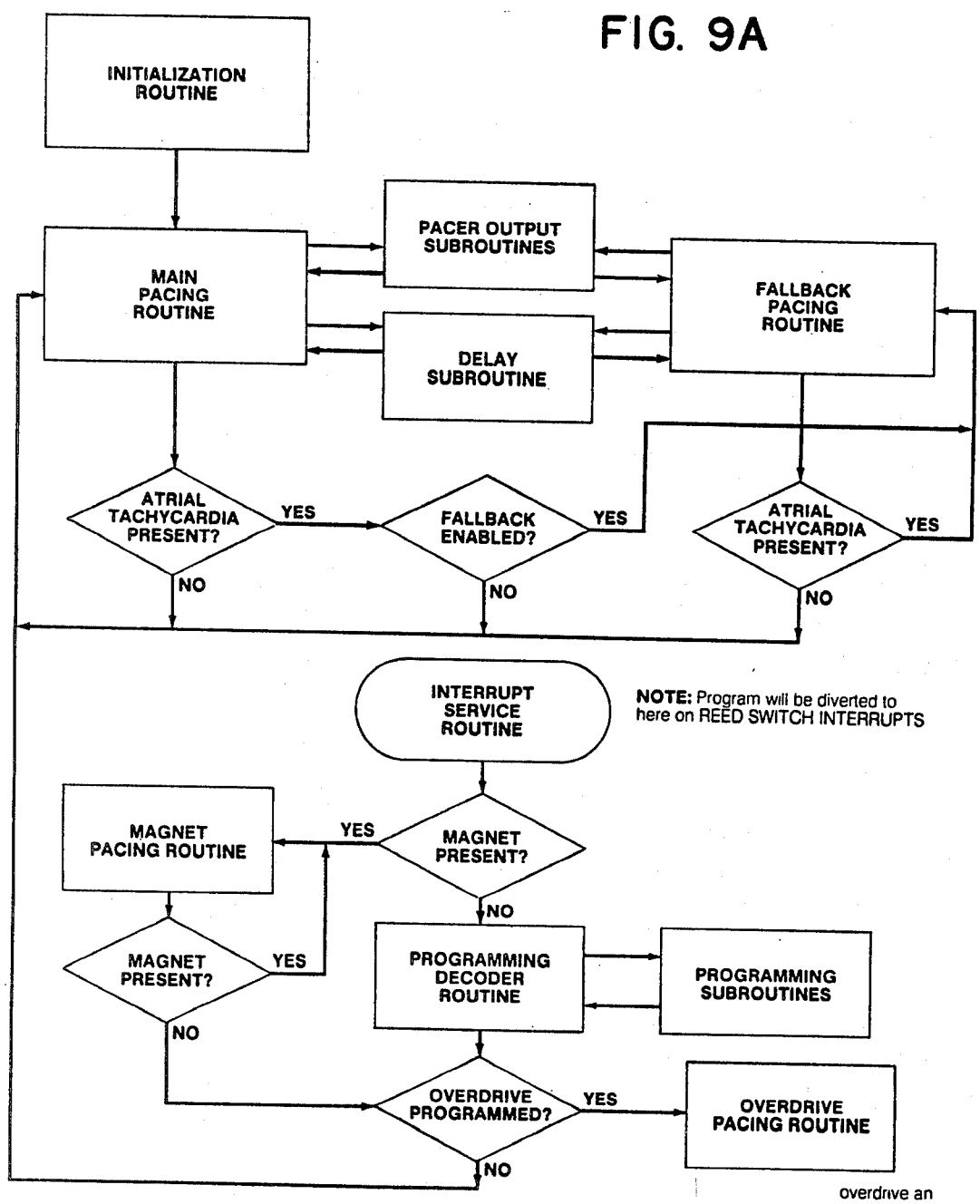
FIG. 9A is a system flowchart.

Appendix I is an annotated assembler listing corresponding to the ROM contents of FIG. 9.

DETAILED DESCRIPTION OF A PREFERRED EMBODIMENT

Figure 1:
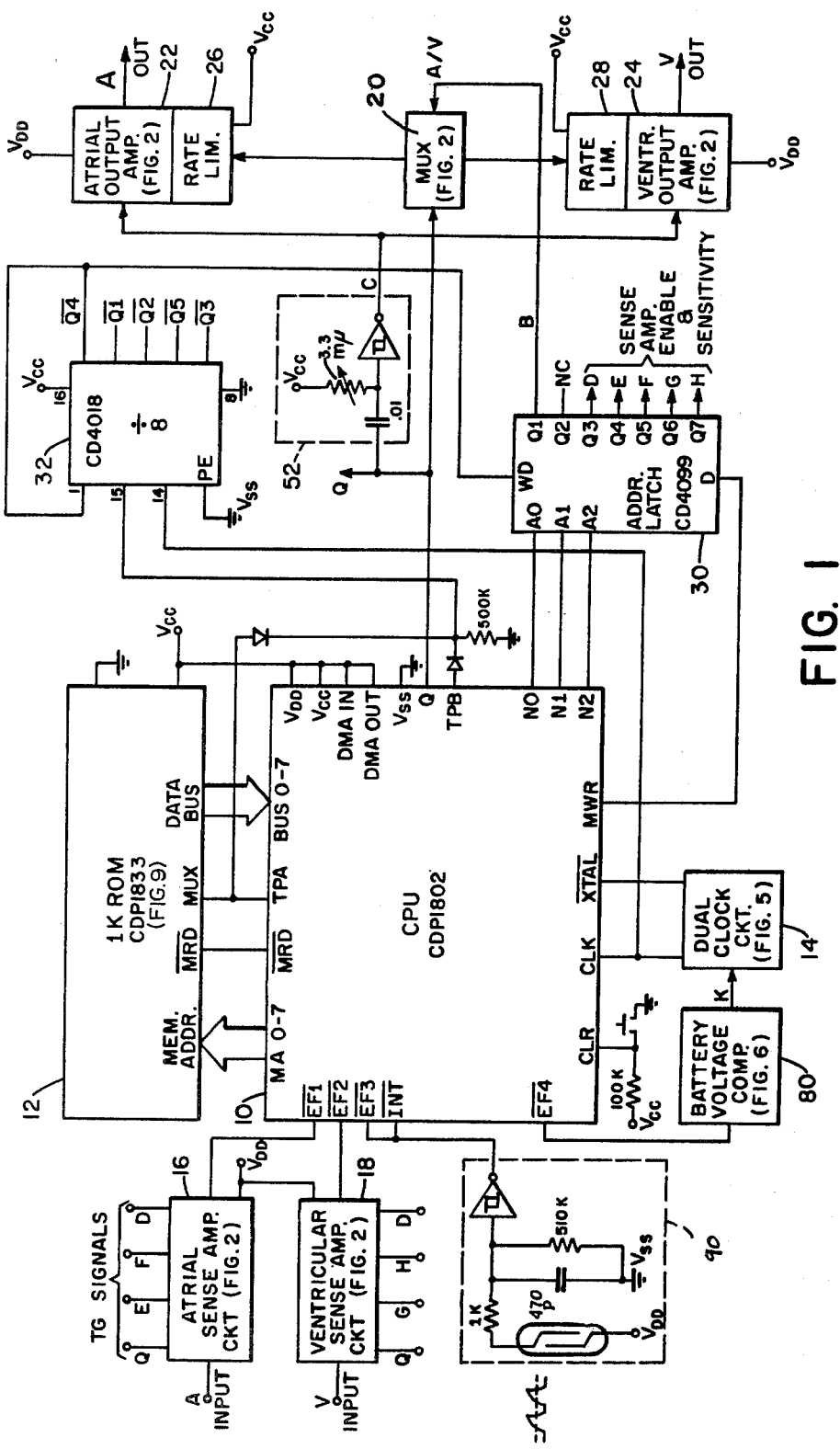
FIG. 1 is a functional block diagram illustrating the electronic circuitry of the cardiac pacer according to the invention.

FIG. 1 illustrates in functional form the overall electronic circuit requirements for pacing and programming in an implantable microprocessor-based multi-mode cardiac pacer according to the invention. The electrical components of the pacer are intended to be powered by lithium compound batteries and sealed together with the battery cells in the customary biologically compatible hermetic enclosure, as in the "Omni Atricor Theta" ™ manufactured by Cordis Corporation, the assignee of the present application. The pacer itself is implanted at a suitable location in the human body and is electrically interconnected with a two conductor pacer lead which terminates perveneously in a pair of electrodes situated respectively in the right atrium and bottom of the right ventricle. The electrically conductive case of the pacer forms the return path or ground electrode in a conventional unipolar electrode arrangement.

The pacer shown diagramatically in FIG. 1 is a microprocessor based pacing system with memory and I/O circuits. The heart of the system is a programmed microprocessor or central processing unit (CPU) 10 in FIG. 1. The RCA CDP 1802 COSMAC microprocessor, a single chip CMOS 8-bit bus-oriented CPU, or equivalent is preferred because of its low power consumption and ample internal scratch pad registers. With the exception of the power supply and a few large components such as the crystal discussed below, the entire system is comprised of integrated circuits preferably divided into a pair of hybrids, one primarily for digital circuitry and the other primarily for analog circuitry. The fixed stored program which operates the CPU in accordance with software instructions is in the read only memory, designated ROM 12 in FIG. 1, comprising 1,024 8-bit bytes in a compatible format such as the RCA CDP 1833. When addressed by the memory address bus (MA 0-7) and enabled via the (MRD)-bar output of the microprocessor, the ROM 12 reads a byte from memory out to the microprocessor via the data bus in the conventional manner.

The system is designed so that the CPU 10 is always in operation, that is, the clock input from dual clock circuit 14 is intended to be continuous. The CPU 10, ROM 12 and clock circuit 14 together with the MA and data buses form a microcomputer. The inputs from the outside world are asynchronous since they are not coupled to the clock frequency of the microcomputer. Asynchronous data may be put into the microcomputer in two distinct methods, via "external flag" or "interrupt". The CDP 1802 has four external flag inputs designated as the complements of EF1, EF2, EF3 and EF4. Spontaneous activity in the atria and ventricles is signalled to the microcomputer via the external flag method. External flags are essentially logic levels which may be tested at a particular point in a software routine by a specific instruction. According to the prescribed state of the flag, the instruction may direct the microcomputer to a special branch of the routine. Programming inputs approach the microcomputer as an interrupt (INT)-bar, the other type of asynchronous input. The microcomputer responds to an interrupt by halting whatever software routine it is executing and jumping to a special interrupt service subroutine. Atrial or ventricular stimulation pulses, on the other hand, are provided synchronously by the microcomputer by multiplexing the 1-bit Q output of CDP 1802 which is set for a programmed number of fetch-execute cycles and then reset.

Sensing and Output Amplifier Stages and Blanking

Inputs indicative of spontaneous cardiac activity are provided by separate atrial and ventricular sense amplifier circuits 16 and 18. The atrial lead terminating in the right atrium forms the input to the atrial sense amplifier 16 whose output is applied to (EF1)-bar of the microcomputer. The ventricular sense amplifier input is formed by the ventricular lead which terminates in the right ventricle. The output of the ventricular amplifier circuit 18 is applied to the (EF2)-bar input to the microcomputer.

The output circuit comprises a multiplexor 20 which directs the Q output of the microcomputer to atrial and ventricular output amplifier circuits 22 and 24 via respective rate limit circuits 26 and 28.

The microcomputer does not have an I/O port as it is normally defined in which data is synchronously output via the CPU data bus. The outputs are synchronous but are done without a port. The "pseudo-port" is provided by an addressable latch 30, preferably I/O decoder CD4099. By this latch, sensitivities are selected, output channels are multiplexed and sense amplifier outputs are blanked. The sense amplifiers 16 and 18 and the multiplexor 20 receive timing or control signals from the addressable latch 30. The addressable latch 30 has eight available outputs, only six of which are used, namely Q1 and Q3-Q7. These outputs correspond to flip-flops which are addressed by the 3-bit I/O lines of the microcomputer, N0, N1 and N2. The I/O lines are low at all times except when an I/O instruction is being executed. The setting or resetting of the addressed output bit is determined by the state of the D input to the latch 30 which is formed by the (MWR)-bar or "write pulse" of the microcomputer. A sampling gate or "strobe" is provided by the input WD to the latch 30. Because of the intricate timing between the command bits and the write pulse, a counter 32, namely CD 4018, performs a divide-by-eight function utilizing the 32 khz microcomputer clock and two timing pulses TPA and TPB ORed together as the data inputs. The output of (Q4)-bar of the counter 32 forms the input to WD sample gate 30. The usefulness of the latch 30 lies in its ability to retain a particular state at each of its output bits until it is ordered to change by the microcomputer. Thus, the latch operates as an outside register.

Latch 30 tells the multiplexor 20 via line B whether to pass the stimulation pulse to the atrial or ventricular output amplifier 22 or 24. Line D blanks the output of both sense amplifiers while lines E, F and G, H, respectively, perform input resistance switching for sensitivity selection.

Transmission gates, Schmitt trigger (inverters), and other logic gates are provided by standard RCA CMOS circuits or the equivalent.

Figure 2:
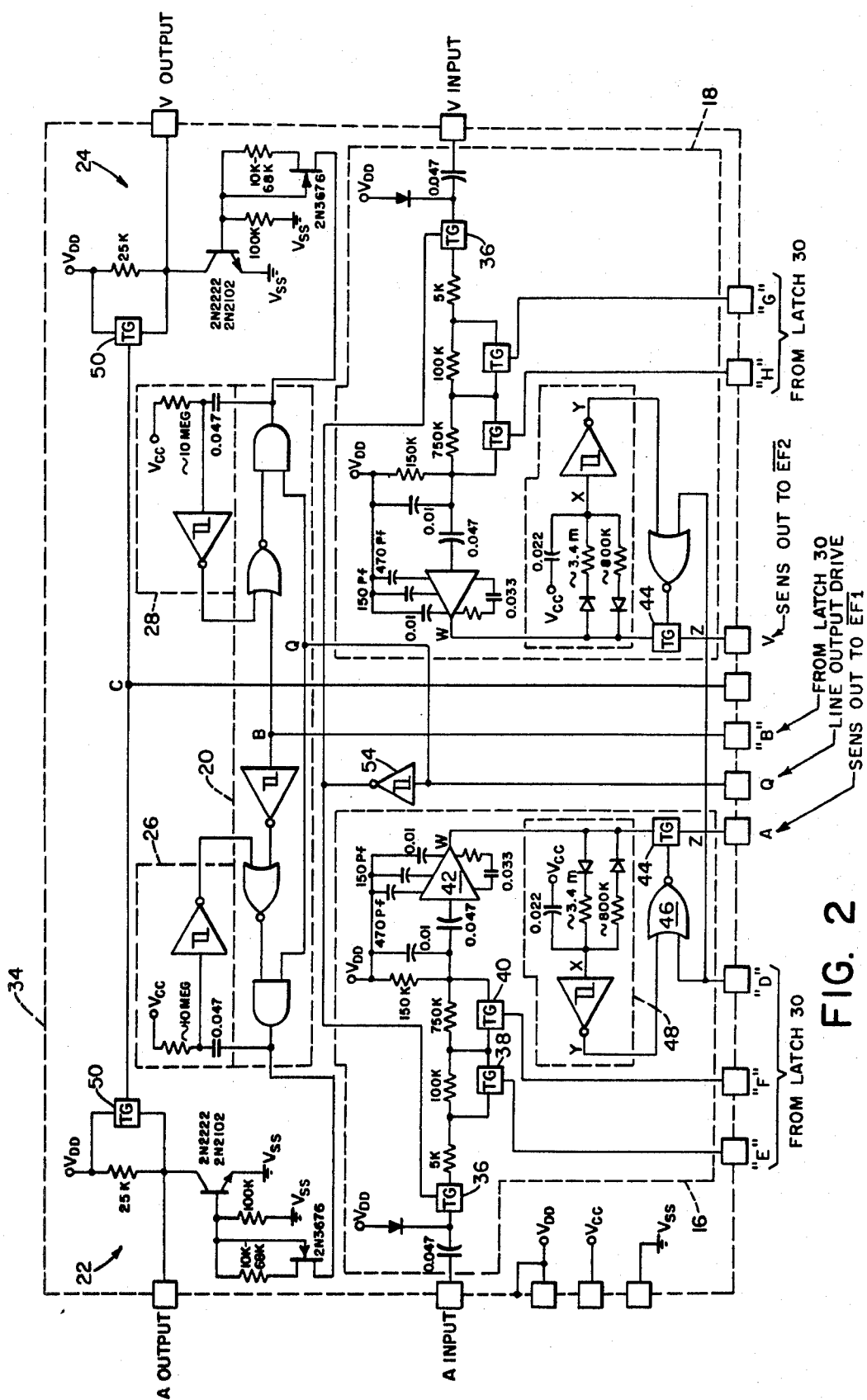
FIG. 2 is an electrical schematic diagram of the analog hybrid circuit containing the atrial and ventricular sense and output amplifier circuits of FIG. 1.

The atrial and ventricular sense output amplifier circuits 16, 18, 22 and 24 along with the multiplexing and rate limiting circuits 20, 26 and 28 for the ouput are incorporated in a single analog hybrid circuit 34 diagrammed in FIG. 2. The sense amplifiers 16 and 18 are symmetrically arranged in the lower half of the circuit diagram of the hybrid 34 while the output amplifier stages 22 and 24 for the atrium and ventricle are at the upper left and right-hand corners of FIG. 22. The electrical components illustrated in FIG. 2 as well as other figures herein where they appear, are illustrated using conventional electrical notation. Values of resistance are given in ohms, for example 1 K meaning 1 kilohm; values of capacitance are given in microfarads unless otherwise indicated. Where two or more values or types are indicated, they are intended to be optional.

Throughout these diagrams the voltages $V_{CC}$, $V_{DD}$, and $V_{SS}$ are consistently used to indicate different nominally fixed levels. Because the pacer of FIG. 1 employs standard off-the-shelf circuitry, the current drain is a constant consideration. One of the ways in which current drain is conserved in this circuit is by creating a second voltage bus to run virtually all of the logic functions, with the exception of the sense amplifiers, noise one-shots and output stages. The nominal battery voltage $V_{DD}$ is 4.26 volts (two-cell lithium battery). The second bus called $V_{CC}$ is nominally 3.5 volts. Since the CDP 1802 and CDP 1833 have a safe operating voltage range which extends below 4 volts, the higher voltage $V_{DD}$ necessary for the amplifier circuits is not essential for the microcomputer, thus, it is replaced by the lower voltage $V_{CC}$. This choice reduces the current drain of the microcomputer system at 32 khz clock rate while preserving full operating characteristics of the amplifier circuits. Sense amplifiers 16 and 18 are internally identical. The lower voltage $V_{CC}$ is not suitable for sense amps because of decreased sensitivity, and would make the output stages more voltage-limited than they now are to deliver 5.5 mA constant-current pulses. Thus they are powered by $V_{DD}$.

The input to sense amplifier 16 from the atrial lead is connected via transmission gate 36 to three serial resistors of progressively larger resistance. After the 5 K resistor, interconnected transmission gates 38 and 40 are arranged to shunt the 100 kilohm and 750 kilohm resistors, respectively. The output of the operational amplifier 42 (a custom Intersil Chip No. BL80003Y previously used in Cordis Omnicor pacers) is passed to the (EF1)-bar input of the microcomputer via transmission gate 44 which is controlled by NOR gate 46. The transmission gates 36, 44 at the input and output, respectively, serve blanking functions while the two internal transmission gates 38 and 40 program the finite sensitivities of the amplifier.

In the atrial amplifier 16 the logic signals E and F from the addressable latch 30 determine whether the resistance in the input is 5 kilohms, 105 kilohms or 755 kilohms. Infinite sensitivity is controlled by software by omitting interrogation of the appropriate sense amplifier. The input transmission gate 36 operates to disconnect the input of the amplifier when the Q line is high, that is, when an output stimulation pulse is being applied on either of the leads. The output transmission gate 44 is arranged to disconnect the output when the D line from the latch 30 is high or when noise is sensed by noise one-shot 48. In the presence of noise above about 45 hertz, the one-shot stays high and inhibits pulses from being passed to the CPU.

Figure 3:
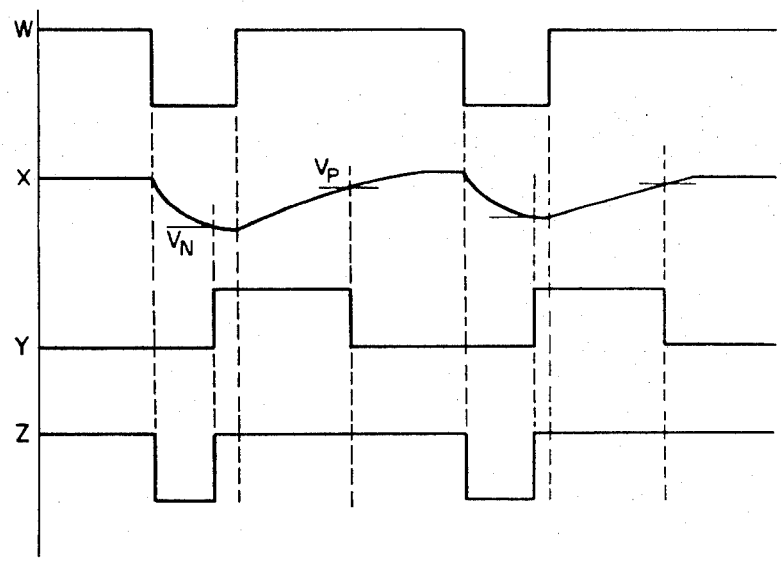
FIGS. 3 and 4 are similar timing diagrams illustrating the response at various points within the sense amplifier circuitry of FIG. 2 to normal and noise sensing, respectively.
Figure 4:
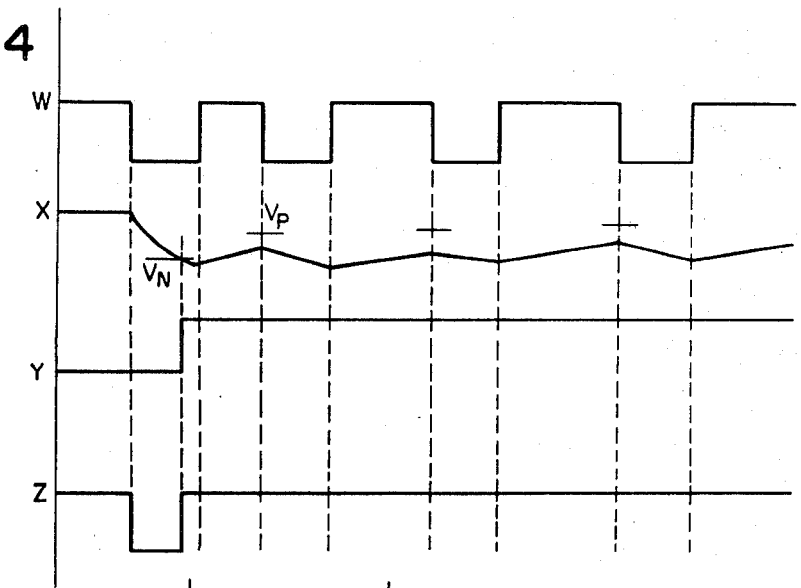

Wave forms appearing in sense amplifier 16 are shown in FIGS. 3 and 4 to illustrate normal response of the amplifier and to block response of the amplifier during noise. Lines W, X, Y and Z in FIGS. 3 and 4 designate corresponding points in the amplifier circuit. Vp is the point at which the output of the Schmidt trigger falls from high to low as shown in line Y. This transition point Vp is not reached when the input signal is too rapid. The result is blocking of the output (Z) as shown in FIG. 4. The output of either sense amplifier is a square pulse of about 20 ms in response to corresponding spontaneous cardiac activity.

Each channel has its own output stage which consists of a constant current controlling JFET and NPN output transistor as shown, for example, for the atrial output amplifier 22 in FIG. 2. The output pulse is amplitude-trimmed to a nominal 5.5 milliamperes (mA) by trimming the JFET feedback resistor. The programmed width of the output pulse determines the intensity of the delivered charge which ranges from 2.75 to 11 microcoulombes per pulse. Pulsewidths are determined in software and come from the CPU via the Q port. The Q signal is switched in accordance with the state of the B signal from latch 30 which controls the multiplexor 20 as shown in FIG. 2. The B signal in the AV sequential mode is addressed and changed by software before each consecutive stimulation pulse.

As a part of the atrial and ventricular halves of the multiplexor 20, a built in rate limiting circuit 26, 28 prevents the pacer from producing stimulating pulses on either channel at a rate faster than approximately 185 beats per minute (bpm). The rate limit circuits 26, 28 are Schmitt trigger retriggerable one-shots which are tuned for approximately 330 ms. Any pulses coming from the CPU at a higher rate will be inhibited. Note that the noise sense and rate limit RC circuits are powered by the lower voltage bus $V_{CC}$ associated with the digital circuitry while the amplifier circuits 16, 18, 22 and 24 are powered at the full battery level $V_{DD}$.

The output of the multiplexor 20 and rate limit circuit 26 on the atrial side, for example, is a logic level 1 which passes through the constant current JFET arrangement to turn on the NPN transistor. The collector, which provides the atrial output stimulation, is connected via a 25 kilohm resistor to $V_{DD}$. The electrically conductive case of the pacer forms a return path for the stimulation pulse and is also connected directly to the battery voltage $V_{DD}$. In practice a large (10 microfarad) capacitor (not shown) is always connected in series with the atrial output and a voltage limiting (e.g., 8.2 volts) zener diode (not shown) is connected in parallel between the case and the capacitively coupled atrial output. The zener diode protects against defibrillators. The same arrangement is used on the ventricular side. The 25 kilohm collector resistor in the atrial and ventricular output resistors are shunted by respective transmission gates 50. These gates are simultaneously controlled by the C line in FIG. 1. The C signal is produced by a one-shot circuit 52 which is turned on for 20 ms by the falling edge of the Q pulse.

Blanking and charge dumping functions are accomplished by controlling the transmission gates 50 in the output circuit and the transmission gates 36 and 44 at the input and output of the sense amplifiers 16 and 18. When the microcomputer determines that it is time to pulse a chamber, the program jumps to a stimulation subroutine. In the transition, the microcomputer puts a logical "1" (high) on the D line, output Q3 of the addressable latch 30 (FIG. 1). As shown in FIGS. 1 and 2 the D line is connected to operate the transmission gates 44 in the output circuits of both sense amplifiers 16 and 18 simultaneously. Thus when the D line goes high the atrial and ventricular inputs to the microcomputer are disconnected or disabled.

When the CPU "sets Q", one of the output channels begins stimulation as directed by latched B line. The Q line is connected via inverter 54 to transmission gates 36 designed to disconnect the inputs to the two sense amplifiers. As the stimulation pulse begins on one of the channels, both sense amplifiers are disconnected to prevent the output stimulation pulse from charging up the sensing networks in the amplifiers. This enables the amplifiers to recover quickly. Without this arrangement the amplifiers are swamped by the larger signal which has an adverse effect on their recovery or settling time. By completely disconnecting their inputs, the sense amplifiers never see the stimulation pulses.

On the falling edge of the Q pulse, the one-shot 52 (FIG. 1) turns on the transmission gates 50 in parallel with the output pull-up resistors. The charge that is accumulated in the output capacitor (not shown) is rapidly "dumped", thereby allowing the sense amplifiers to recover more quickly due to low offset voltages on the electrodes.

Meanwhile, on the falling edge of the Q pulse, the sense amplifier input transmission gates 36 are opened to reconnect the amplifiers to the atrial and ventricular leads. Approximately 56 ms after the Q pulse began, the microcomputer tells the addressable latch 30 to reset the D line. This causes the output transmission gates 44 to reconnect the sense amp outputs to the external flags of the microcomputer. The foregoing blanking functions work together to prevent cross talk between channels which could possibly lead to undesirable inhibition of output pulses.

Clock System and Low Battery Indicator

Figure 5:
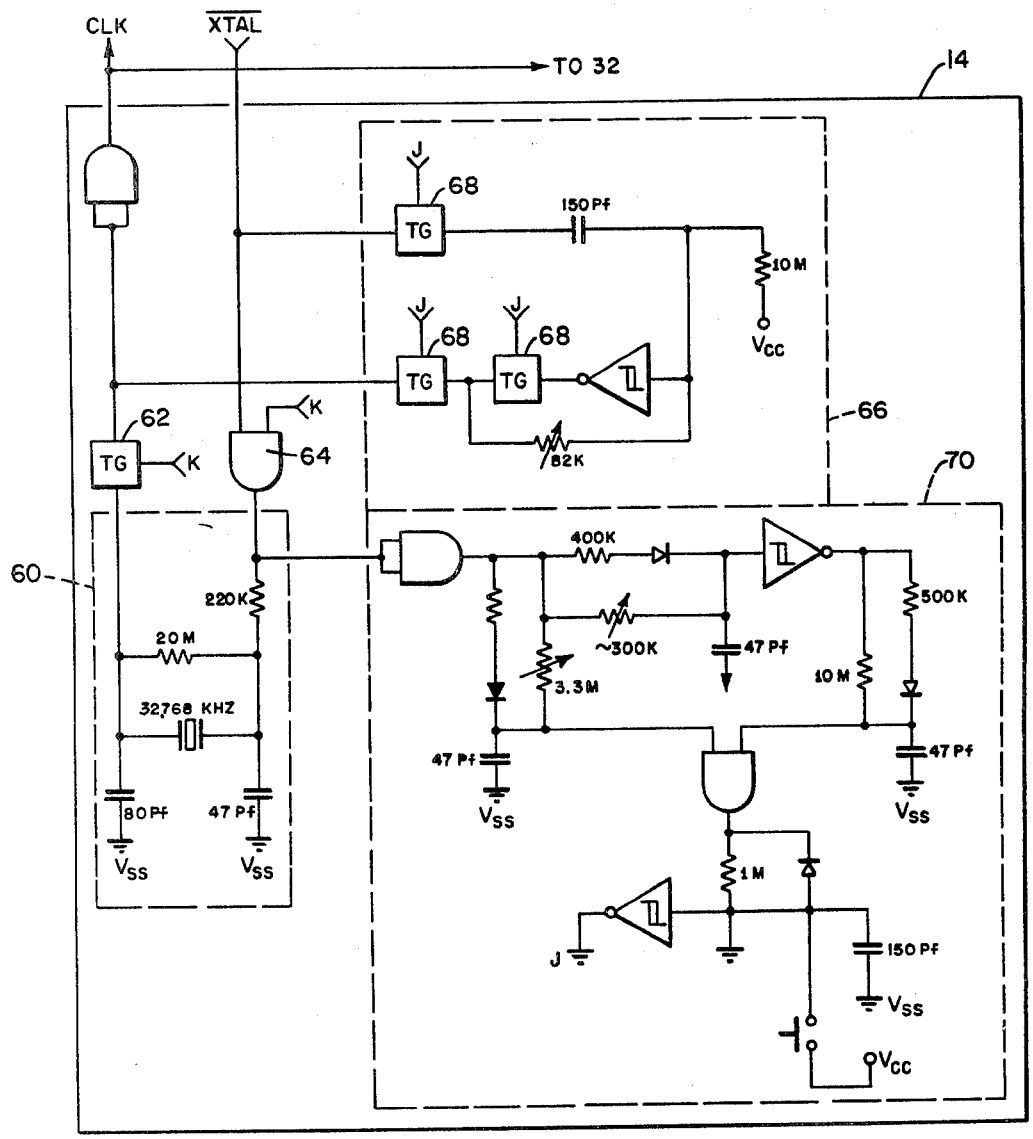
FIG. 5 is an electrical schematic diagram of the dual clock circuit of FIG. 1.

The CPU requires an external oscillator or clock to step it through instruction sequences. The pacer of FIGS. 1 and 2 employs two alternative clocks. As shown in FIG. 5, the dual clock circuit 14 includes a crystal oscillator 60 connected as the main clock to the clock input of the CPU via a normally conducting transmission gate 62. The main clock utilizes a 32.768 khz crystal with stabilizing capacitors. The crystal oscillator can be turned off by the high output of the AND gate 64 whose input is connected to (XTAL)-bar. A backup oscillator is provided by a Schmitt trigger RC oscillator circuit 66 tuned to approximately 31.1 kHz at full battery voltage. Note that the oscillator circuit 66 is energized by the lower voltage bus $V_{CC}$, nominally 3.5 volts. A group of three transmission gates 68 serve to enable and connect the RC oscillator to the CPU clock input.

The crystal is an extremely stable oscillating element typically varying by by less than two or three parts per million. However, should the crystal fail for catastrophic reasons such as mechanical shock or excessive moisture, it most probably will either begin oscillating in harmonic multiples of resonance (i.e., 65.536, 98.304 kHz, etc.), or it will stop altogether. Such a failure could produce drastic results in pacer performance but is easily detected as a gross change in frequency by the frequency detection circuit 70 in FIG. 5. When the frequency detection circuit 70 senses the crystal oscillator output is outside of the range of about 4 kHz to 48 kHz, the logic output K and its complement J cause the RC oscillator 66 to be substituted for the crystal oscillator 60. The K signal disconnects the crystal oscillator 60 from the CPU by means of the transmission gate 62 and disables it via the AND gate 64. The J signal activates and connects the RC oscillator 66. This substitution will cause all of the timing functions to be slowed by at least five percent. The slowing factor would be approximately five percent only if the battery was at its full rated voltage since the RC oscillator is voltage sensitive. A variation of this magnitude in the output is easily detected by the physician by observing the magnet rate. Once the RC oscillator is substituted, it will remain in the circuit indefinitely since the frequency detector 70 will find that the crystal oscillator output is zero, i.e., outside the acceptable range.

Figure 6:
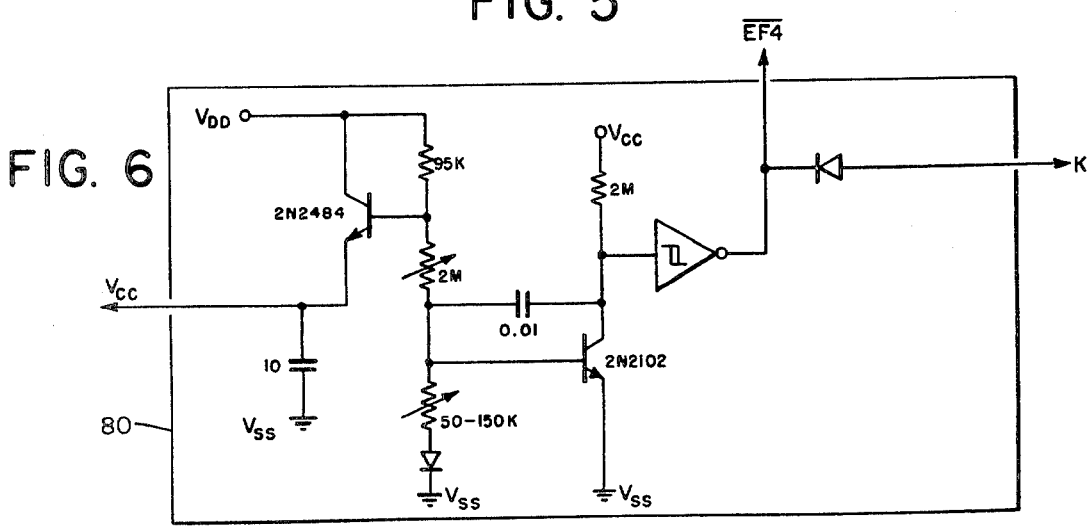
FIG. 6 is an electrical schematic diagram of the battery voltage comparator circuit of FIG. 1.

The logic K signal can also be produced by the battery voltage comparator 80. As shown in FIG. 6 the comparator circuit 80 comprises a critically biased transistor circuit and a Schmitt trigger 84. The emitter of the first NPN transistor (2N2494) serves to energize the $V_{CC}$ bus. The second transistor (2N2102) is biased in such a way that it is conducting at 4.26 volts and thereby presents a low input to the Schmitt trigger. When the battery voltage $v_{DD}$ falls to about 3.85 volts between first and second plateaus of the discharge profile, this biasing network shuts the second transistor off (not conducting) and the Schmitt trigger output goes from high to low. The output of the Schmitt trigger produces a K signal which is phantom ORed with the K signal from the frequency detector circuit 70. This signal from the battery voltage comparator causes the main crystal oscillator to be disconnected from the clock input and disables the main oscillator via the AND gate 64. Since the frequency detector 70 senses that the crystal oscillator is off, it also presents the J logic output which activates the RC oscillator 66.

Figure 7:
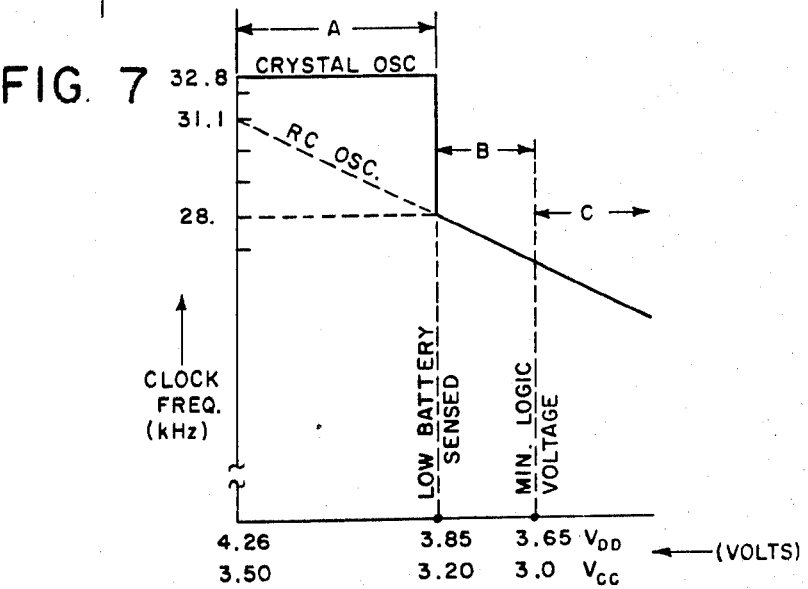
FIG. 7 is a graph of clock frequency versus declining battery voltage.

As shown in FIG. 7 the battery voltage circuit 80 causes the clock frequency for the microcomputer to fall from the nominal 32.8 kHz value to the output frequency of the RC oscillator when battery voltage $v_{DD}$ is below 3.85. This produces about a fifteen percent drop in the output frequency. In the good voltage region designated A in FIG. 7, where the battery voltage $v_{DD}$ is above 3.85 volts, the crystal oscillator frequency will govern the microcomputer unless there is a catastrophic failure. If the crystal oscillator frequency is outside of the acceptable range and the battery voltage is still in range A the RC oscillator will be switched in at 28 to 31 kHz depending on the battery voltage level. As the voltage decreases from 3.85, the microcomputer is operated by the RC clock. The battery voltage eventually reaches a point where the low voltage bus $V_{CC}$ for digital circuits is below 3.0 volts, the minimum safe operating voltage for the CDP 1802 thus there is defined a second region B for low battery operation with the RC oscillator. Below region B a third region C exists where the battery voltage is insufficient to ensure viable operation of the microcomputer at the available clock frequency.

In the dual clock circuit 14 as shown in FIG. 5 the frequency detection circuit 70 has a pushbutton switch which is used to start the crystal oscillator at the factory. The pushbutton switch merely symbolizes the application of a voltage level and is done during final assembly and testing by momentarily jumpering the K output of the frequency detector to the $v_{CC}$ bus. The CPU is initialized at the factory in a similar manner by momentarily grounding the clear terminal as indicated in FIG. 1.

Programming is accomplished via a reed switch circuit 90 (FIG. 1). An RC filter network and a Schmitt trigger help shape the programming pulses. The external programmer is an electromagnetic impulse programmer (not shown) which produces a saw tooth flux versus time waveform as shown to the left of circuit 90 in FIG. 1. The dashed line represents the threshold level at which the reed switch contacts close. This level is dependent of course on the proximity of the external programmer to the pacer. The Schmitt trigger output goes to the interrupt terminal and external flag (EF3) inputs of the CPU, where software then decodes and accepts or rejects programming codes. The software bandpass frequency is designed for nominal 330 hertz programming pulses. Besides the electromagnetic programmer, the reed switch is also responsive to a permanent magnet. If the external flag (EF3)-bar stays high for a longer period of time than it would normally stay high for programming pulses, the CPU assumes that a permanent magnet has been applied and goes into the "magnet rate" routine which provides fixed rate AV sequential stimulation. Except for the reed switch, the crystal and the analog hybrid circuits 16 through 28 (FIG. 2), all of the circuitry in FIG. 1 is preferably included in a single digital hybrid.

Parameters

Table I gives the nominal parameter values of the pacer of FIG. 1.

TABLE I

|  | Available Nominal Values | Values in Stat Set Mode (VVI) |
|---|---|---|
| Output current, mA | 5.5 | 5.5 |

TABLE I-continued

|  | Available Nominal Values | Values in Stat Set Mode (VVI) |
|---|---|---|
| (fixed) | | |
| Output Voltage (open circuit), V (fixed) | 4.2 | 4.2 |
| Atrial tachycardia response mode | 2.1 Block or Fallback | 2.1 Block* |
| Ventricular refractory period, ms (not programmable) | 291 | 291 |
| Atrial Refractory period, ms | 305 or equal to programmed max. rate interval | programmed max. rate interval* |
| AV Delay, ms | 80 120 165 250 | 120* |
| Minimum pacing rate, ppm (determines minimum rate interval) | 50 60 70 80 | 70 |
| Maximum atrial rate (determines maximum rate interval) | 100 130 160 180 | 160* |
| Fallback rate, ppm (determines final minimum rate interval in fallback mode) | 55 65 75 85 | 75* |
| Ventricular Sensitivity, mV | 0.8 1.5 2.5 Off | 1.5 |
| Atrial Sensitivity, mV | 0.8 1.5 7.0 Off | Off |
| Ventricular pulse duration, ms | 0.5 1.0 1.5 2.0 | 1.5 |
| Atrial pulse duration, ms | Off 0.5 1.0 1.5 | Off |

*Inapplicable in STAT SET VVI but retained in other modes unless specifically reprogrammed.

The software is designed to automatically start the pacer off in the ventricular-inhibited (VVI) mode with "standard values" indicated in right-hand column of Table I. The output current is fixed at 5.5 mA while the voltage is determined by the load. Refractory periods when the output of the sense amplifier is ignored are both fixed and identical except when 2:1 block is selected in which case the atrial refractory period equals the programmed maximum rate interval.

There are four distinct modes of operation, as indicated in Table II below: ventricular-inhibited (VVI), atrial-synchronous ventricular-inhibited (VAT delta+VVI), atrial-synchronous without ventricular-inhibited (VAT delta) and atrial-inhibited, atrial synchronous ventricular-inhibited (DDD). The symbol "x" indicates that the variable parameter is programmed to a finite value.

TABLE II

| Parameters | VVI | VDD (VAT + VVI) | VAT | DDD (AAI + VAT + VVI) |
|---|---|---|---|---|
| Atrial Output Pulse Duration | Off | Off | Off | x |
| Atrial Sensitivity | Off | x | x | x |
| Ventricular Output Pulse | x | x | x | x |

TABLE II-continued

| Parameters | VVI | VDD (VAT + VVI) | VAT | DDD (AAI + VAT + VVI) |
|---|---|---|---|---|
| Duration | | | | |
| Maximum Rate | NA | x | x | x |
| Fall Back Rate | NA | x | x | x |
| A-V Delay | NA | x | x | x |
| Ventricular Sensitivity | x | x | Off | x |
| Minimim Rate | x | x | x | x |

Timing

Figure 8A:
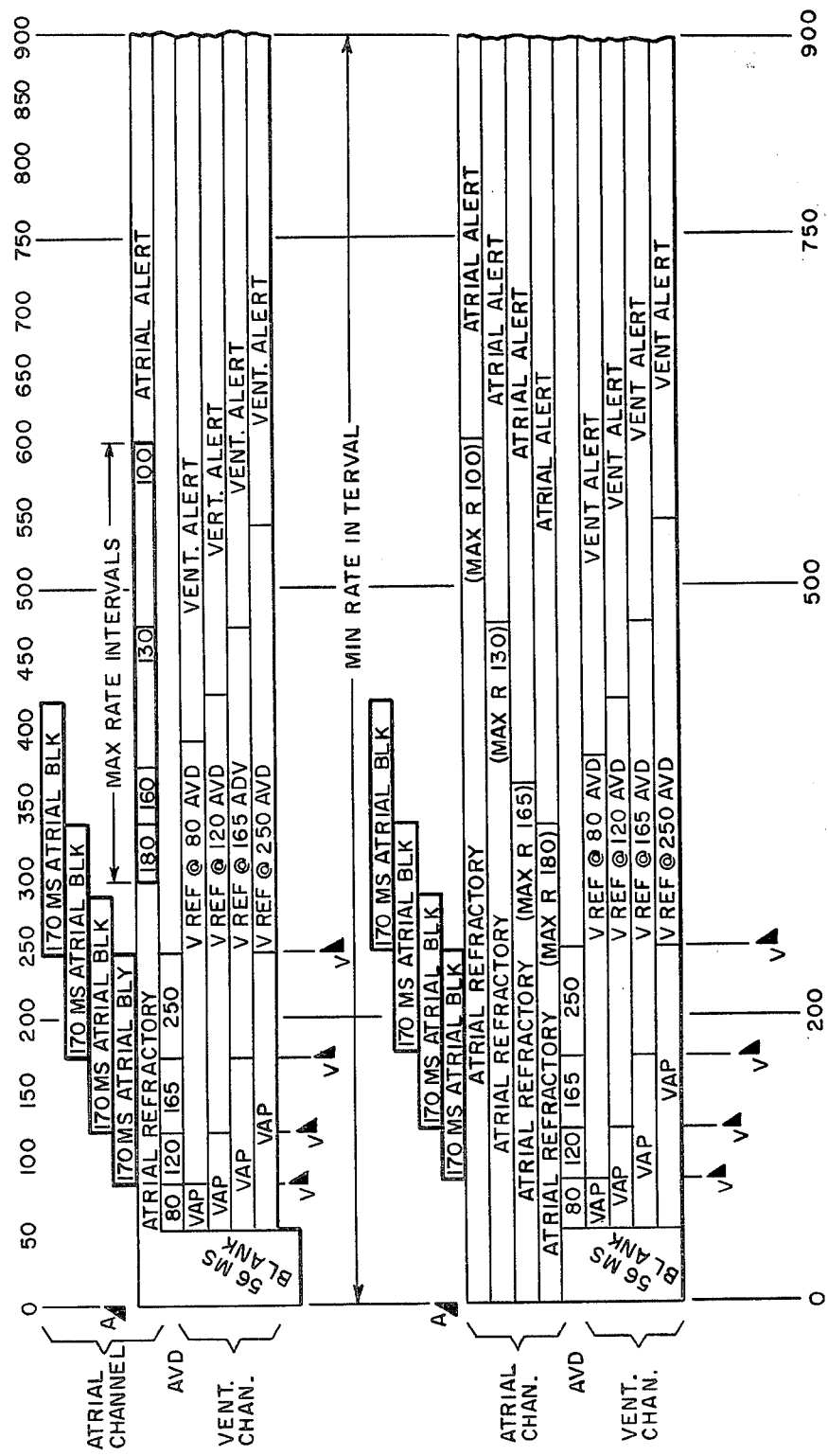
FIG. 8 is a composite three-part timing diagram, parts 1 and 2 of which illustrate the atrial and ventricular timing for DDD pacing with fallback or 2:1 block mode, respectively, selected as the tachycardia response in the main pacing routine; part 3 illustrates timing in the fallback pacing mode.
Figure 8B:
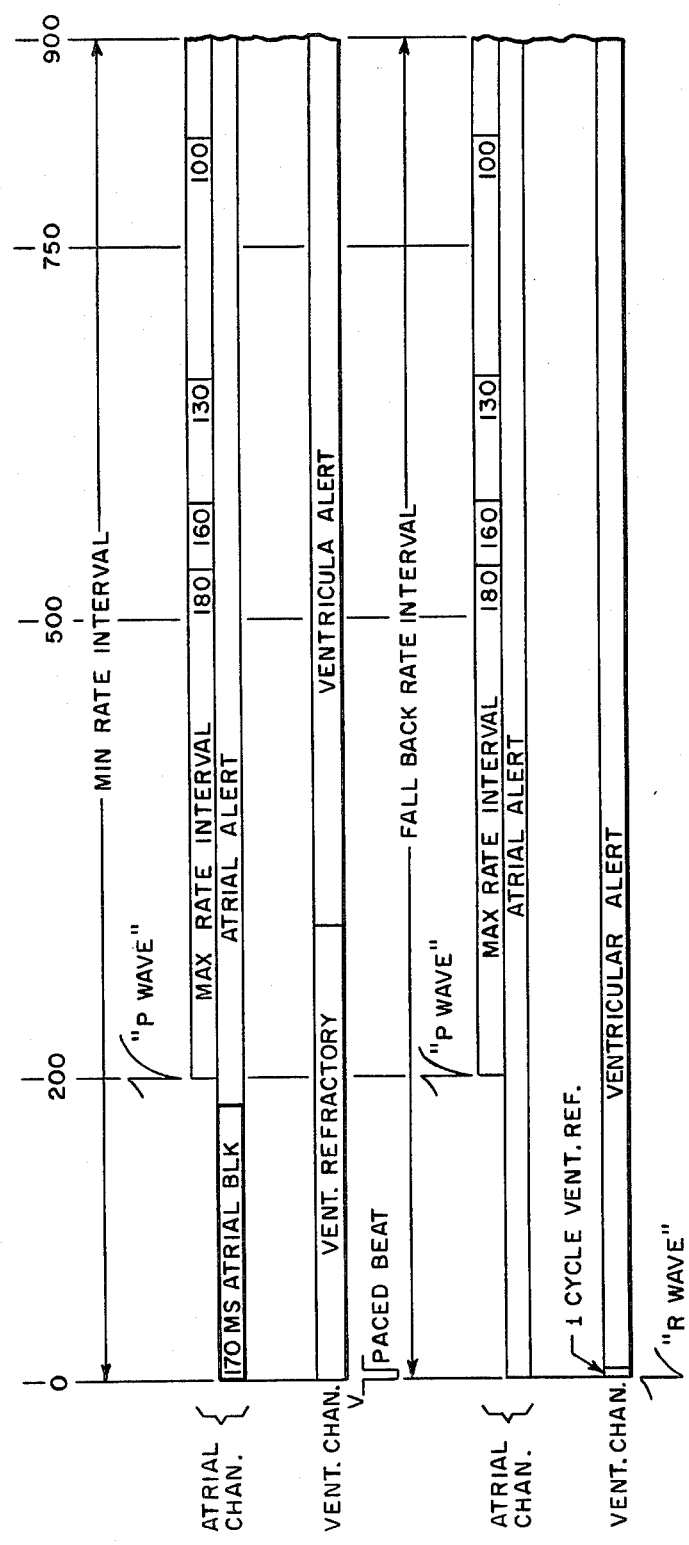
Figure 10:
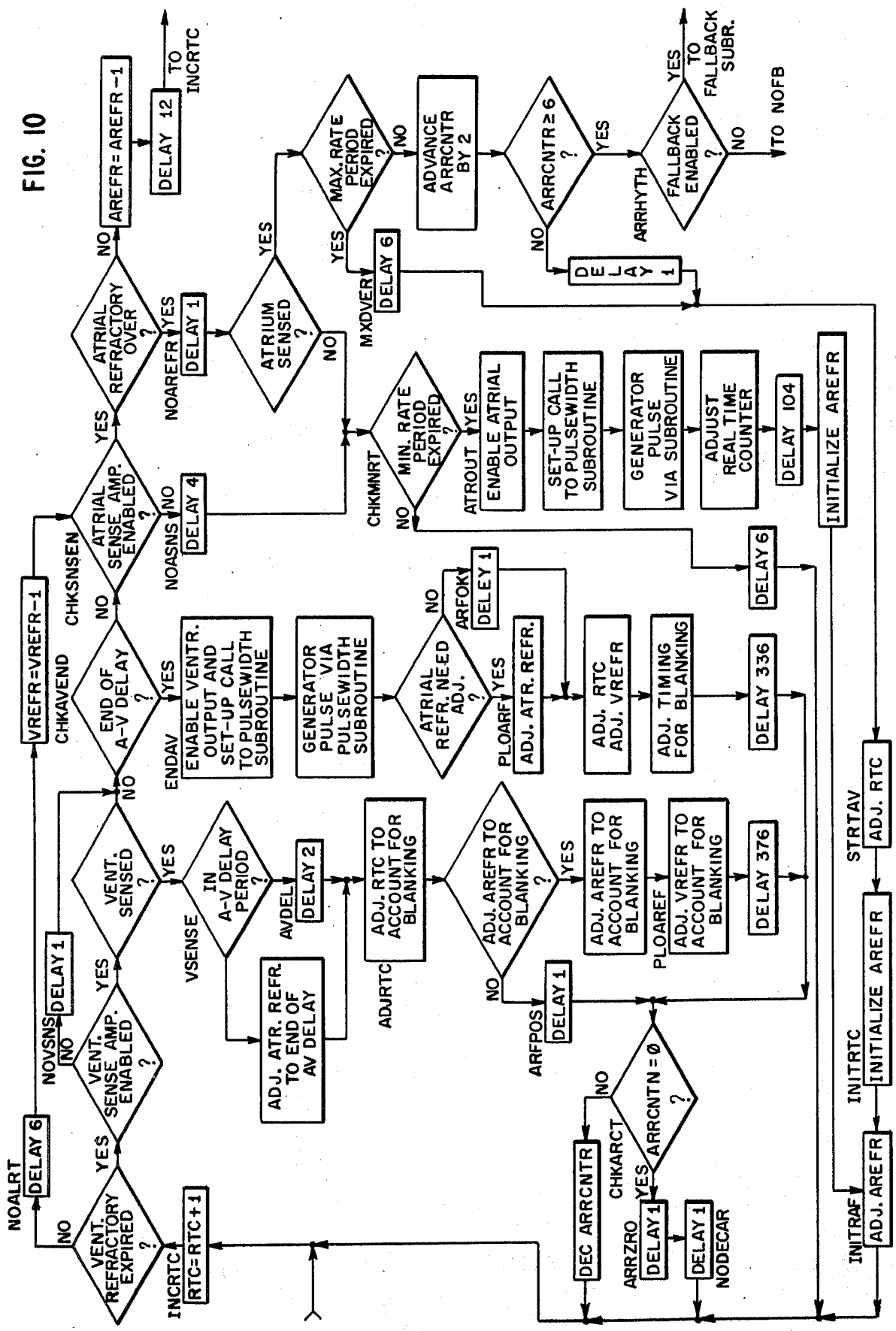
FIG. 10 is a flow chart of the main pacing routine.
Figure 11:
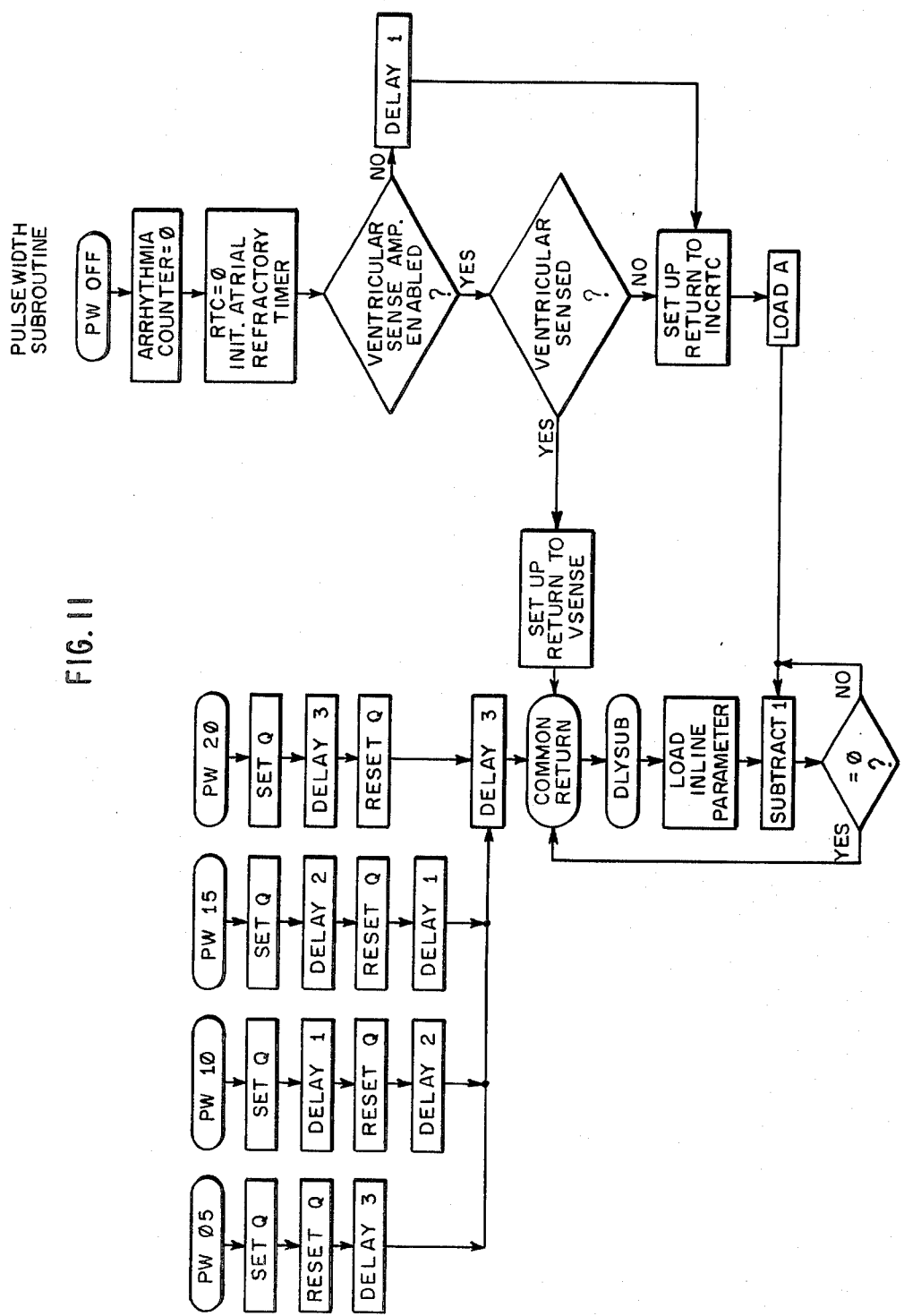
FIG. 11 is a flow chart of the pulsewidth subroutine.

FIG. 8 sets forth the basic timing relationships employed by the main pacing routine of FIG. 10. The minimum rate interval is the pulse-to-pulse interval in the minimum programmed rate. When the spontaneous or intrinsic atrial rate is below this rate as in bradycardia, the pacer will produce stimulation pulses at the programmed minimum rate (e.g. 70 bpm). The full AV sequential mode in bradycardia and heart block illustrates the case when slow or absent atrial and ventricular activity calls for stimulation on both channels.

The timing cycle for each channel consists of a refractory period and an alert period. The refractory periods are both fixed at 305 ms (except in 2:1 block mode) and occur after either sensed or stimulated activity. During the refractory period, the affected channel cannot respond to any input received.

Ventricular stimulation causes (170) ms blanking in both channels via the software. In addition, ventricular sensing blanks the atrial channel. Atrial stimulation causes 56 msec. blanking. The AV delay is timed by software. If the programmed AV delay elapses before spontaneous ventricular activity, the ventricles are stimulated. After an output pulse, the CPU commences a ventricular refractory period. Meanwhile, in the atrial channel the expiration of the atrial refractory period begins the atrial alert period in which the CPU monitors the atrial lead for a P-wave. If the entire minimum rate interval goes by without sensing a P-wave, the CPU calls the programmed stimulation subroutine for the atria. After blanking, the ventricular alert period resumes sensing. If no ventricular activity appears by the end of the next AV delay, the CPU issues a ventricular pulse. If normal AV conduction occurs resulting in ventricular contraction before the end of the AV delay, the ventricular output is inhibited and the ventricular channel becomes refractory.

The maximum rate interval is used in detecting atrial tachycardia and therefore only applies to the atrial channel. Except in fallback mode, this channel is off during VVI pacing. The maximum rate interval places a ceiling on the intrinsic atrial rate which the pacer will follow. If atrial pulses are so fast that they regularly precede the maximum rate interval, the pacer automatically enters the fallback pacing routine or executes 2:1 block, depending on which response mode is programmed.

Software

The real life identity of the pacer of FIG. 1 is found in the software (in ROM sometimes referred to as "firmware") contained in the program memory. Each byte in ROM 12 is conventionally represented by two hexadecimal "hex" digits. FIG. 9 shows the contents of ROM 10 in groups of four hex digits representing two bytes of memory at neighboring memory locations. Memory locations are arranged consecutively row by row from right to left and top to bottom. Most of the ROM bytes are instructions from the standard repertoire of the CDP 1802 system; some of the bytes represent data or parameters. All of the ROM bytes are fixed; they can only be read, not changed.

The sixteen 16-bit internal registers within the CDP 1802 are used for variables. Table III below contains a list of the register assignments, the registers being indicated by hex code from zero through F. For example, "5.1" and "5.0" designate the high and low bytes of register 5, respectively.

TABLE III

CPU Register Assignments

R0=Main program counter (MPC)
R1=Interrupt subroutine program counter (INT)
R2=Dedicated data pointer to lookup table (PNTR)
R3=Atrial tachycardia or arrhythmia counter (ARRCNTR)
R4=Dedicated subroutine program counter (SUB)
R5=R5.0 Fallback loop counter (LPCNTR); R5.1 Fallback steps (STEP)
R6=R6.0 Used to calculate check sum (ROM); R6.1 Ventricular sense enable flag (VSNSFLG)
R7=R7.0 Fallback timer (FBTMR); R7.1 Atrial sense enable flag (ASNSFLG)
R8=R8.0 Real time clock (RTC)
R9=R9.0 Atrial refractory period counter (AREFR); R9.1 Atrial refractory data
RA=RA.0 Ventricular refractory data period counter (VREFR); RA.1 Ventricular refractory data
RB=RB.0 Programming pulse counter (PPC)
RC=RC.1 Fallback disable flag—2:1 block (FBFLG)
RD=RD.0 Low order address of ventricular pulsewidth subroutine (VNTPW)
RD.1 Low order address of atrial pulsewidth subroutine (ATRPW)
RE=RE.0 Low order address of AV delay (AVDLY); RE.1 Low order address of Fallback rate (FBRATE)
RF=RF.0 Low order address of Minimum rate (MNRATE); RF.1 Low order address of Maximum rate (MXRATE)

Appendix I is an annotated assembler printout corresponding to the ROM code in FIG. 8. The first column on the left in Appendix I provides the memory location in hex digits. The second column indicates the hex digits corresponding to he binary machine code. The third column in from the left provides program location mnenonics or labels such as "SUMLOOP" which mark a particular location of interest in the ROM, particularly, the destination of a branch or the starting point of a routine or subroutine. The next column gives a translation of the machine code into assembly language followed by the operand. Annotations preceded by semicolons or asterisks are provided to explain the functions of the instructions or to identify the subroutine.

As shown in FIG. 9B, software for the pacer disclosed herein consists of the following modules:
1. Initialization routine
2. Main pacing routine
3. Fallback pacing routine.
4. Pacer-output routines.
5. Delay subroutine.
6. Interrupt service routine.
  a. Programming-pulse decoder.
  b. Programming-subroutines.
  c. Magnet pacing routine.
7. Ventricular-overdrive pacing routine.

Initialization Routine

This routine is executed on inital reset and whenever STAT SET is programmed. When the batteries are installed, the CPU cleared and the oscillator started, the CPU automatically begins executing instructions from the ROM address 0000 (Appendix 1, FIG. 9). After an interrupt in which STAT SET is programmed, the microprocessor returns to the inital ROM location by loading the zero address in the main program counter before returning from the interrupt service routine. In either event, the microprocessor is instructed to initialize the 16 internal CPU scratch pad registers (Table III) for VVI pacing at 70 bpm, 1.5 ms output pulsewidth and 1.5 mv sensitivity. The atrial sense amplifier and output circuit are disabled until programmed by the physician.

A ROM test check sum routine is included as a part of the initialization routine. This self check sum loop provides an improved means of facilitating production testing. If the sum of the contents of all ROM locations is not correct, the digital hybrid will not operate. The checksum test takes place prior to initialization of the registers. When the checksum test fails, the pacer stops at instruction memory location 12 H (the letter "H" designates hex digits) with the Q output "permanently" set. Thus, testing the Q output will instantly reveal a ROM disorder.

The initialization routine disables the atrial sense amplifier by resetting the atrial sense enable flag (R7.1). Ventricular sensitivity is selected by instructions which reset the G line (Q6) from the addressable latch 30 in FIG. 1 and set the H line (Q7) of the latch to determine the input resistance of the ventricular sense amplifier in FIG. 2. The address of the appropriate stimulation subroutine for the 1.5 ms ventricular pulsewidth is loaded into register RD.0. Since in the VVI mode, no atrial stimulation is needed, the address of a "dummy" stimulation routine is loaded into the atrial stimulation pointer RD.1. Similarly, the addresses of the data for maximum rate, minimum rate and standard AV delay are entered. In addition the 2:1 block option is preselected by setting the fallback disable flag RC.1. The program immediately enters the main pacing routine having set up all of the necessary standard values in accordance with Table 1 during the initialization routine.

Main Pacing Routine

The main pacing routine can operate in any of eight pacing modes:
1. DDD—dual demand AV sequential.
2. VDD—atrial synchronous, ventricular inhibited.
3. VVI—ventricular demand.
4. DVI—"bifocal" AV sequential.
5. VOO—ventricular asynchronous.
6. DOO—asynchronous AV sequential.
7. VAT—atrial asynchronous
8. DAD—atrial synchronous, ventricular asynchronous The DDD dual-demand AV sequential mode provides maximum physiological interaction with the heart. Sensing and pacing is provided from both atrial and ventricular chambers. DDD closely resembles the "normal" rhythm of the heart and is thus known as "physiological pacing". The other seven modes are realized by interdependently disabling either sense amplifier and/or the atrial output as in the VVI mode, with a dummy stimulation subroutine which takes up the same time that a genuine pulse would take, but never sets the Q output of the CPU.

The main pacing routine is flow charted in FIG. 10. This routine is responsible for timing four intervals: the refractory period, AV delay, maximum rate, and minimum rate intervals. Tests for atrial and ventricular activity, if appropriate and if so programmed, determine whether to execute atrial or ventricular stimulation pulses. Except in VVI or 2:1 block mode, the main pacing routing keeps track of the number of atrial tachycardia events sensed between the end of the absolute atrial refractory period and the end of the maximum rate interval and determines whether to exit the main pacing routine and go to the fallback routine to respond to atrial tachycardia.

There are three timekeepers in the main pacing routine: the real time clock (RTC) implemented by regularly incrementing R8.0; the ventricular refractory period register RA.0 and the atrial refractory period register R9.0.

Timing intervals are gauged in two fundamentally different ways. The minimum rate interval, maximum rate interval and AV delay are timed by comparing the RTC count with programmed numbers. The refractory periods on the other hand are kept track of by the equivalent of separate presettable down counters: namely the atrial and ventricular refractory registers R9.0 and RA.0. For each kind of timing function however, the increments or decrements are synchronized at the rate of once per scan cycle.

The main pacing routine works as a plurality of equal length, alternate, parallel, diverging and reconverging instruction sequence loops all passing through a common instruction INCRTC at which the real time clock is incremented by 1. This instruction begins a "scan cycle." A single scan cycle is defined as the time required by the CPU to make one pass through the main pacing routine via one of the alternate loops. The scan cycle time is dependent on the clock rate. In the case of the 32.8 kilohertz clock which normally applies, a scan cycle takes 14.16 ms. The scan cycle time defines a sampling rate short enough to detect intrinsic cardiac activity.

From the location INCRTC, there is a labyrinth of decision loops all of which return to INCRTC. During each scan cycle, decisions must be made by the microprocessor as follows:
1. Has ventricular-refractory period expired?
2. Is ventricular sensing enabled?
3. Has ventricular sensing occurred?
4. If ventricular activity was sensed, was it during AV delay?
5. Is it time for a ventricular output?
6. Has atrial ventricular refractory expired?
7. Is atrial sensing enabled?
8. Has atrial sensing occurred?
9. If atrial activity is sensed, is it after the maximum rate?
10. Should fallback response be initiated?
11. Is it time for an atrial output?

No matter what sequence of decisions and actions are taken, exactly 29 instructions must be fetched and executed, consuming 58 machine cycles and 14.16 msec. at the crystal frequency. Real time is constantly maintained by the software. Thus each timing parameter will be subject to a 14.16 ms range (i.e., a programmed 165 ms AV delay may range from 158 to 172) as each amplifier is sampled once during a scanning cycle.

The delay subroutine is frequently called to consume idle CPU time in order to equalize the loop length to maintain real time operation so that the RTC is incremented at the rate of once per scan cycle.

After incrementing RTC, the CPU next determines whether the pacer is in the ventricular refractory period by testing the ventricular refractory register. This register like the atrial register is pre-loaded with a number corresponding to the refractory period which is fixed at 305 ms unless the 2:1 block mode is selected in which case the atrial refractory period is equal to the programmable maximum rate interval. If the ventricular refractory counter is not at zero, it is decremented once per scan period. During the initialization routine the ventricular register is set at zero thus starting the pacer off in ventricular alert (FIG. 8). In ventricular alert, the CPU asks if the ventricles are to be sensed by testing the ventricular sense enable flag R6.1. Ventricular activity is sensed by testing the EF2 input for ventricular activity. If there is none, the main routine proceeds to determine whether it is the end of the AV delay period by seeing whether RTC equals the AV delay designated by RE.0. If it does and no ventricular activity has been sensed, the program jumps to produce a ventricular output according to the programmed pulsewidth. When the microprocessor determines that it is time for a pacer output in this manner, it selects the proper channel using the "channel select" output bit (B-line). Next, the CPU register containing the programmed pulsewidth data is used to determine which output subroutine should be called. The address of the appropriate subroutine is computed and loaded into the subroutine program counter which then takes control. The output subroutine produces a pacer output at the programmed pulsewidth and the end of the pulse triggers the charge dump circuit which depolarizes the pacing electrode. Upon returning from the output subroutine, the corresponding refractory period is reloaded into the refractory register and a blanking period is established during which the sensing inputs are ignored. The delay subroutine is called to consume the blanking time. After blanking has expired, the program resumes scanning as before.

If the RTC indicates that it is still before the end of the AV delay, the CPU checks to see whether the atrial sense amplifier is enabled. If atrial sensing is disabled, as it would be in the VVI mode, the CPU proceeds to determine whether the minimum rate interval has expired. If it has, the dummy atrial output subroutine is called. If the minimum rate has not yet expired, the CPU returns to the INCRTC instruction via an appropriate delay.

In pacing modes requiring atrial sensing, the CPU would instead first check the atrial refractory register and decrement it if it was not zero before returning to the INCRTC instruction. If the atrial refractory period is over, on the other hand, the atrial sense amplifier would be checked via EF1. Unless atrial activity is actually sensed at the time of this scan, the CPU would proceed to check the minimum rate interval by examining the RTC and returning via an appropriate delay to INCTRC or enabling an atrial stimulation pulse if the minimum rate has expired. Alternatively, if atrial activity is sensed, the CPU determines whether the maximum rate period has expired. If it has, then the sensed atrial event is given full credit by resetting the RTC to a number equivalent to zero and reestablishing the atrial refractory period.

The main pacing routine causes the atrial channel to be blanked by disabling the atrial sense amplifier whenever intrinsic ventricular activity is sensed as well as whenever either channel is stimulated. In addition the atrial blanking period is 170 ms instead of 56 ms to prevent possible atrial sensing of ventricular depolarizations.

Blanking occurs on both channels simultaneously whenever an output stimulation pulse is produced on either channel. In addition, blanking takes place on the atrial channel whenever a ventricular event is sensed to prevent cross sensing. Whenever blanking occurs, it is accomplished by way of output signals via the addressable latch to the gates at the outputs of the sense amplifiers. Since this blanking time period coincides with the initiation of a refractory period on at least one channel, the refractory periods are automatically adjusted by instructions in the main pacing routine to take into account the time already consumed by blanking. In addition, the RTC is adjusted to account for blanking since the blanking instructions in effect idle the main pacing routine for a period of several scan cycles. This is important when the atrial sense amplifier is blanked upon sensing intrinsic ventricular activity.

The ventricular and atrial refractory periods are different. If the fallback mode is enabled (no 2:1 block), the atrial refractory is set at 305 ms. This absolute refractory period places a 197 bpm tachycardia response limit. This upper limit reduces the probability of inadvertent fallback initiation. The ventricular refractory period is one scan cycle shorter than the atrial refractory period when fallback is enabled to eliminate the possibility of inhibiting ventricular outputs due to a ventricular refractory longer than the atrial refractory period.

The main pacing routine also monitors atrial tachycardia. The physician may select either fallback or 2:1 block as the atrial tachycardia response. If 2:1 block is programmed, the atrial refractory period is automatically set equal to the maximum rate interval. Thus in the 2:1 block mode, which is automatically preselected by STAT SET, the CPU is bound to find that the maximum rate interval has expired if the atrium has been sensed. If the intrinsic atrial rate exceeds the maximum rate, every second P-wave will fall in the refractory period and not be sensed.

If fallback is selected as the atrial tachycardia response, a more complex recognition scheme is employed. Although the atrial refractory period is absolute, if an atrial pulse is sensed between the end of the atrial refractory period and the end of the maximum rate interval, it is treated as a potential atrial tachycardia. The CPU employs the arrythmia counter R3 to keep track of the relative frequency of atrial tachycardia. If an atrial sense output occurs during a scan cycle when the maximum rate interval has not yet expired, the arrythmia counter is incremented twice. The same counter is decremented once whenever ventricular activity is sensed or ventricular output is generated. Thus the CPU makes a weighted value judgment to classify atrial tachycardia. Whenever the arrythmia counter accumulates a count of six or more, the fallback response mode begins as the program branches to the fallback pacing routine.

Fallback Pacing Routine

The fallback pacing routine flow charted in FIG. 12 provides VVI pacing at an initially faster gradually decreasing rate during atrial tachycardia. Since AV sequential pacing is not appropriate during an atrial tachycardia episode, the pacing mode is automatically changed to VVI when the fallback routine is entered. This results in disassociation of the atria and ventricles. The ventricular rate is gradually decreased until the programmed fallback rate is achieved, while atrial activity is monitored to determine when the tachycardia ceases so that the program may return to the main pacing routine and, for example, resume AV sequential pacing. The arrhythmia counter is used to determine when normal pacing should resume. Whenever atrial activity is sensed before the maximum rate interval has expired, during the fallback routine, the arrythmia counter is set equal to a full count of six, while ventricular sensing and pacing events decrement it by only one. When the arrythmia counter reaches zero, the program branches back to the main pacing routine.

The technique of incrementing the arrhythmia counter by six instead of by two establishes a hysteresis relationship between entering and exiting the fallback routine. The tachycardia classification requirements are made less stringent once the CPU has decided to enter the fallback mode. While six ventricular stimulation pulses in a row without an atrial tachycardia will clear the arrhythmia register in the fallback mode, a single tachycardia resets the arrythmia counter to six requiring an additional six tachycardia-free pacing cycles. Once the arrhythmia counter does become cleared, the CPU will exit the fallback mode on the next scan cycle. Once out of the fallback mode, the more stringent requirements for atrial tachycardia classficiation are reinstituted, in which the sensing of a single fast atrial pulse before the expiration of the maximum rate interval is only doubly weighted. It now takes six cardiac cycles each having at least one atrial tachycardia event for the arrhythmia counter to achieve the full count of six in order to classify the behavior as arrhythmia, while in the fallback mode it only takes one atrial tachycardia event to maintain the arrhythmia status.

The fallback routine begins at a rate slightly below the maximum rate. Every 3.6 seconds, the rate is decreased by 14.16 ms until it reaches programmed fallback rate. It then remains at this rate until the arrhythmia counter reaches a count of 2. At this time the R—R interval is lengthened by an amount greater than the blanking period following a ventricular output to ensure that P-waves are not being hidden by atrial blanking. In the present pacer embodiment the blanking period is set at 170 ms and in the amount by which the R—R interval is increased at the arrhythmia count of "2" is 240 ms. This avoids the predicament where the atrial tachycardia rate is near twice the fallback rate and every second P-wave is hidden by the atrial blanking period making the pacer unable to determine the actual atrial rate.

The lengthened R—R interval shifts the phase of the R-waves relative to the P-waves so the pacer may accurately determine the true atrial rate before deciding whether to exit fallback. Thus the lengthened R—R interval restrains the pacer from prematurely exiting from the fallback operation due to the inability to detect P-waves at or near twice the fallback rate. The same phenomeon is employed to advantage in the 2:1 block mode where the P-wave which occurs so fast that it is within the maximum rate interval is ignored.

After two more tachycardia-free pacing intervals following the lengthened R—R interval, the arrythmia counter reaches zero and the program branches back to the main pacing routine. In returning to the main pacing routine, the RTC is loaded with the value of the AV delay before the CPU returns to the INCRTC instruction in the main pacing routine. This is necessary and proper because the fallback pacing routine will have just issued a ventricular pulse.

Scan cycles of 14.16 ms are used in the fallback routine as in the main pacing routine. The decisions required during a fallback scan cycle are:
1. Has fallback rate been achieved (loop counter at zero)?
2. Is arrhythmia counter equal to 2?
3. Is arrhythmia counter equal to zero?
4. Has atrial sensing occurred?
5. If atrial activity is sensed is it faster then the maximum rate?
6. Is ventricular sensing enabled?
7. Has ventricular sensing occured?
8. Is it time for a ventricular output?

The delay subroutines are called by the fallback routine whenever necessary.

When the CPU reaches the programmed fallback rate, assuming that it stays in the arrhythmia routine long enough, it will continue to operate as a VVI pacer at the fallback rate indefinitely so long as tachycardia is sensed.

Pacer Output Subroutines

There are five pacer output subroutines: one for each programmable pulsewidth (off, 0.5, 1.0, 1.5, and 2.0 ms). The Q output of the microprocessor is set for the duration of the pulsewidth, thereby energizing the constant current output amplifier circuit to generate a pacer output stimulus. The trailing edge of the output pulse activates the charge dump circuit which depolarizes the pacing electrodes. In order to maintain real time operation (i.e. RTC incrementing at the rate of once per scan cycle), each of the subroutines requires twelve instruction cycles (24 machine cycles) including the calling sequence, regardless of the output pulsewidth (including zero). The same subroutines are used for either channel except that the ventricular pulsewidth can be anything but off and the 2 ms pulsewidth is dedicated to ventricular stimulation.

Delay Subroutine

The delay subroutine is called frequently by the pacing routines to equalize branch execution times so that all possible passes through the pacing routine consume 29 instructions (58 machine cycles) to standardize the scan cycle time. Generally, if the time required to perform tasks in one branch is less then the time required for another branch with which it will converge, the delay subroutine is called. A parameter that specifies the number of instruction cycles needed is passed to the subroutine through the accumulator in the CPU.

Interrupt Service Routine

Figure 13A:
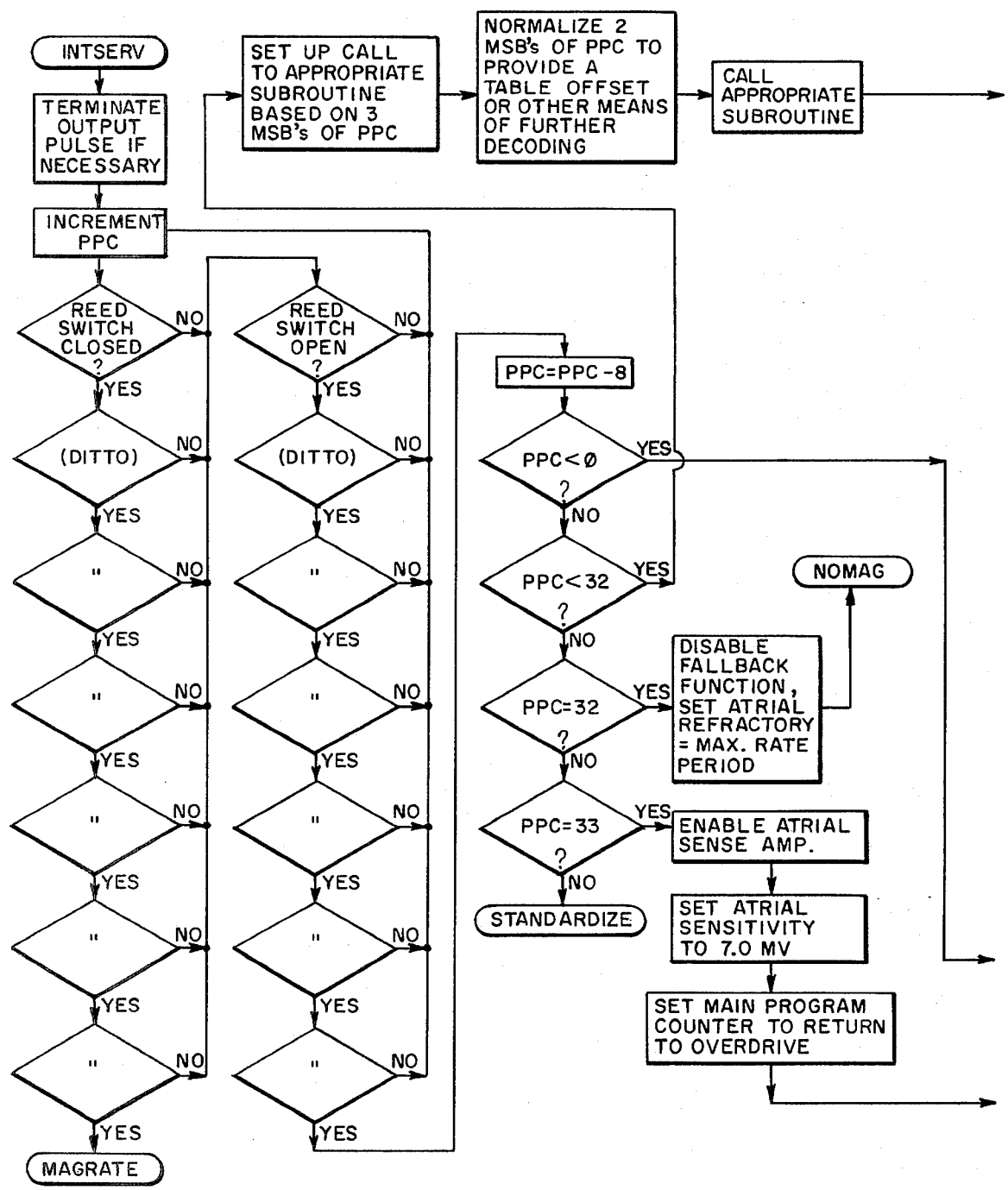
FIG. 13 is a flow chart of the programming interrupt service routine.
Figure 13B:
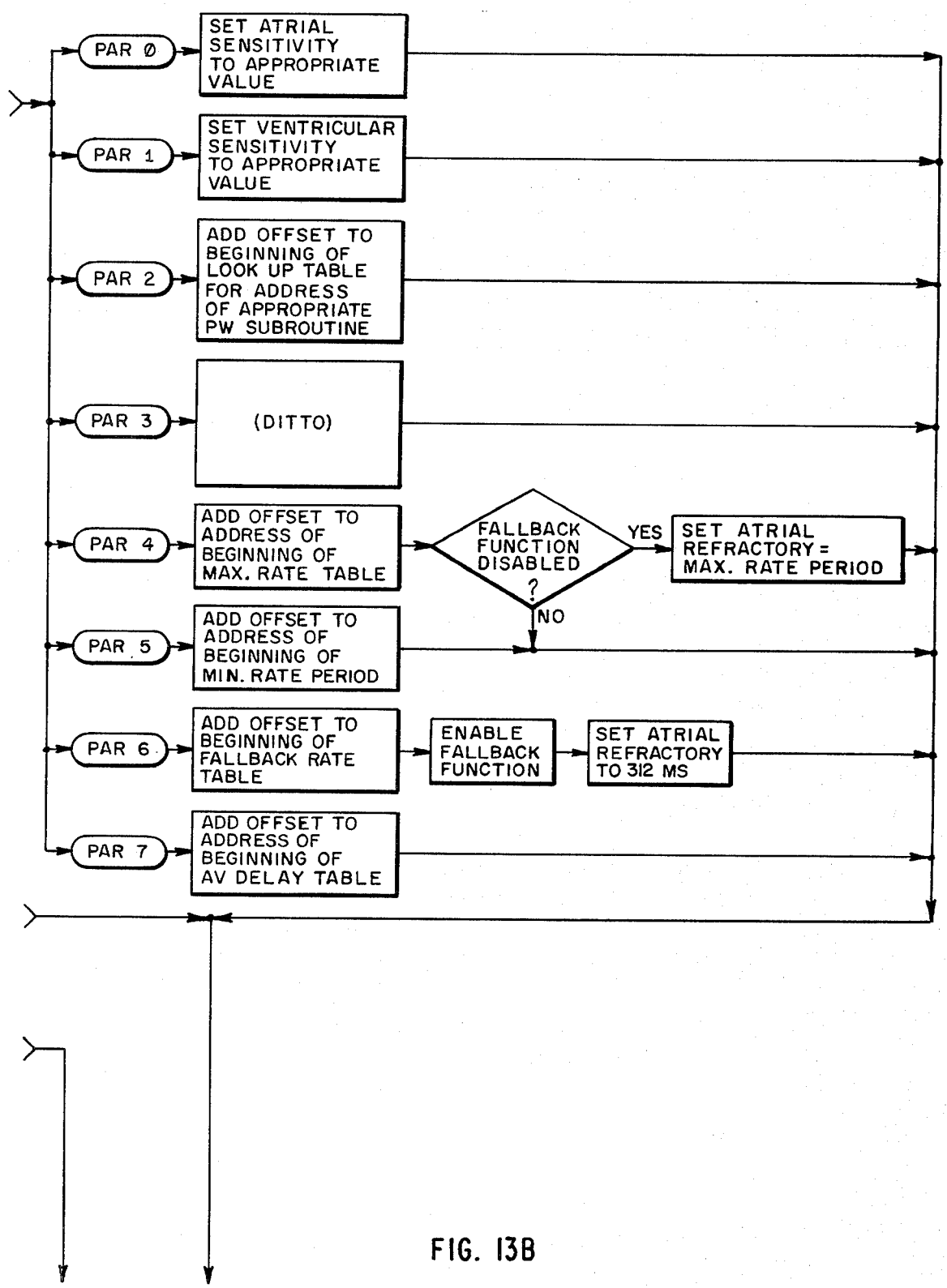
Figure 13C:
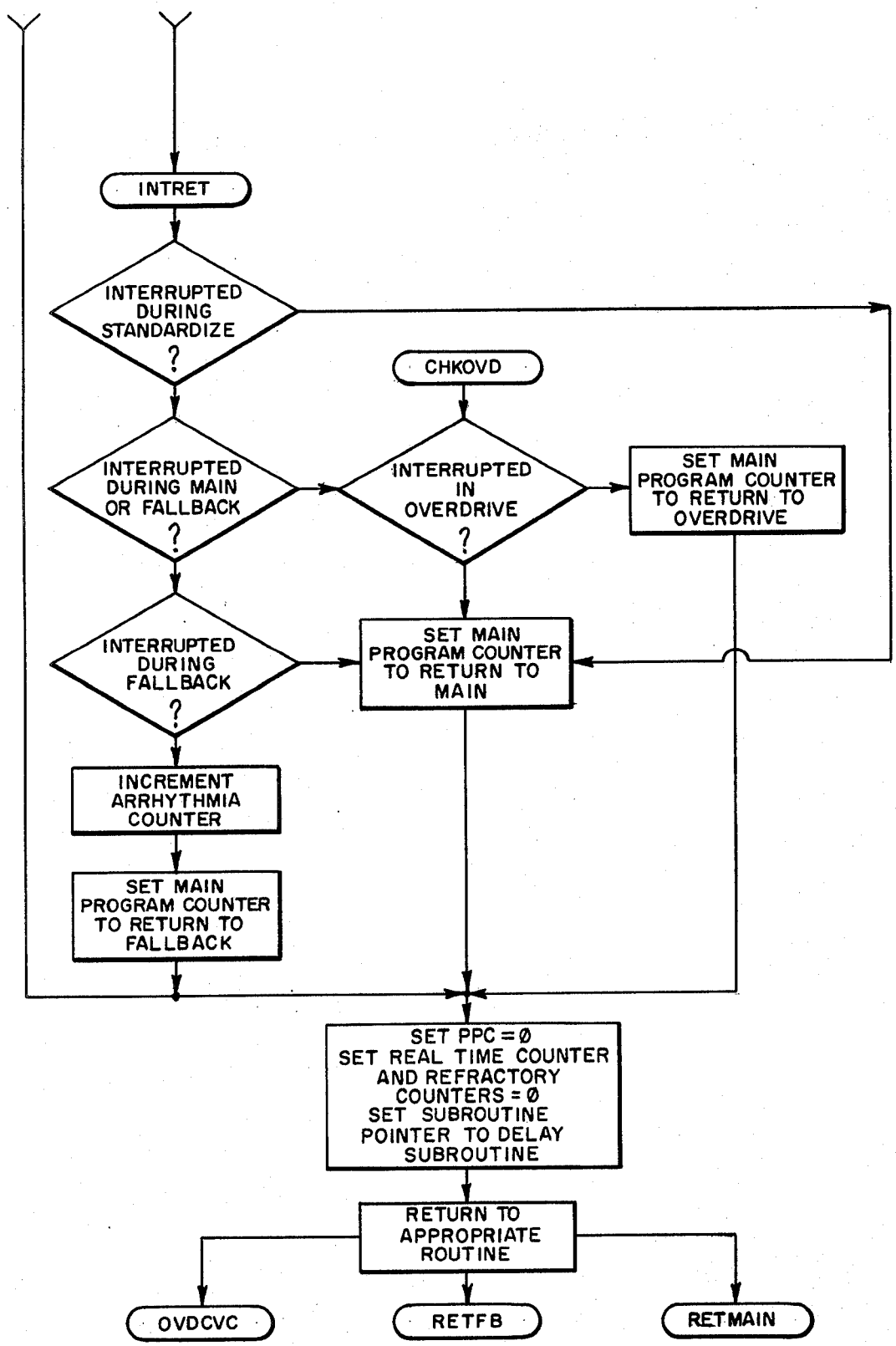

Reed switch closure (via programming the pacer or magnet application) will interrupt program execution in any pacing routine and transfer control of the CPU to the interrupt service routine flow charted in FIG. 13. When the reed switch closes, the interrupt request input to the CPU is enabled, causing program flow to be suspended after completion of the instruction in progress. A dedicated CPU register which contains the address of the interrupt service routine then becomes the program counter. Since an interrrupt may occur at any place in the program, certain precautions must be taken. The first instruction in the interrupt routine resets the Q output so that in case the interrupt occurs during a pacer stimulus, the stimulation pulse will be terminated first. In addition, real time is not maintained during interrupt processing and sensing is ignored. When returning from an interrupt, the pacer timing cycle is reinitialized to a point as if a ventricular event had just occurred. This allows the pacer time to sense intrinsic activity before the next stimulus occurs to avoid competition with intrinsic rhythms. The selection of this point also insures that the pacer will have the maximum possible time to synchronize with the patient's intrinsic cardiac activity.

Programming is accomplished by any Cordis Corporation Model 222B programmer using the program card shown in FIG. 14 for reference. The program is encoded by turning a knob on the right of the programmer to one of the eight parameters indicated on the front of the card and selecting the value A, B, C, or D by turning the left knob. After these two settings are made and the middle slide switch is down, the program button on the programmer is depressed. The programmer automatically emits a train of a predetermined number of magnetic impulses at 333 Hz. The number of pulses is counted in the pacer and decoded by software to determine the programmed parameter and value. Because of the software bandpass in the microcomputer system of FIG. 1, only programmers with a 333 Hz pulse train are acceptable. Programmers using a 666 Hz pulse train will misprogram the pacer.

In addition to programming parameters such as output pulsewidth, the programmer has several optional modes which can be accessed: ventricular overdrive, STAT SET and 2:1 block (fallback disable).

The interrupt service routine is divided into the following modules:
1. Programming pulse decoder (FIG. 13).
2. Programming subroutine (FIG. 13).
3. Magnet pacing routine (FIG. 16).

Programming Pulse Decoder

The microprocessor's programming input is EF3. Through the use of software instructions that allow branching on either state of programming port (reed switch open or closed) the pulses may be counted. The resulting count is checked for validity and decoded to determine which parameter is being altered and the value of the new parameter. Lookup tables are used for this process.

If the count received through the programming port is between eight and 39, eight is subtracted and the result is treated as a five-bit code. The three least significant bits determine which of the eight parameters is to be altered, while the two most significant bits indicate the new parameter value. Thus, a two dimensional lookup scheme is employed.

The first lookup table is a list of addresses of the eight programming subroutines. There is one subroutine corresponding to each programmable parameter. The three bits of the programming code form the address of the subroutine needed for the particular parameter being programmed. This address is used to initialize the subroutine program counter after which the call is executed.

The second phase of the lookup process is performed by the programming subroutines themselves.

Counts outside of the eight-39 range are handled differently. Less then eight pulses is invalid and rejected by the software. Counts greater then 39 pulses are used to program 2:1 block (fallback disable), ventricular overdrive and STAT SET (standard values) as follows:

40 pulses—2:1 block
41 pulses—ventricular overdrive
42 or more pulses—STAT SET

The software checks for these special codes before the look up scheme is employed. If 2:1 block is programmed, a flag is set in CPU register R.1 which disables the fallback response mode. In addition, the atrial refractory period is set equal to the programmed maximum rate interval. Thus for atrial rates greater than the maximum rate, 2:1 AV block results. Programming of any fallback rate will re-enable the fallback response by resetting the flag and reducing the atrial refractory to 305 ms.

Ventricular overdrive is selected by turning over the program card in FIG. 14 and setting the knobs to the appropriate value. The middle switch pushed to the farthest up position selects overdrive.

When ventricular overdrive is programmed, the atrial sensivity is automatically reset to 7.0 mv and the program returns to a special overdrive pacing routine rather than the main pacing routine.

For counts of more then 41 pulses, the program automatically branches to the initialization (STAT SET) routine in which all the parameters are set to internally preestablished standard values. All other programming is done via the programming subroutines.

Programming Subroutines

As shown in FIG. 9B, programming subroutines are called by the foregoing programming pulse decoder routine. Each programmable parameter has its own subroutine for loading the corresponding register as follows:

1. Atrial sensitivity;
2. Ventricular sensitivity;
3. Atrial Pulsewidth;
4. Ventricular Pulsewidth;
5. Maximum Rate;
6. Minimum Rate;
7. Fallback Rate; and
8. AV Delay.

A separate interrupt cycle is necessary to call each of the parameter value subroutines. Thus to reprogram all eight parameters to other than standard values, eight separate interrupt cycles are necessary. Each parameter has four possible values. The two most significant bits of the codes derived from the programming pulse count determine which of the four values is being programmed.

The sensitivity programming subroutines are responsible for controlling sensitivity outputs. The state of these bits is determined by a two bit code.

In the pulsewidth programming subroutines, the two bit code is used as an index to look up the address of the appropriate pacer output subroutine from a table. This address is then stored in the CPU register used to determine output pulsewidth for the appropriate channel. Dedicated CPU registers are also used to store the minimum rate, maximum rate, fallback rate, and AV delay.

The minimum rate and AV delay subroutine use the two bit code to look up the parameter value and store it in the dedicated CPU register for that parameter. Maximum rates and fallback rates of subroutines do this as well, however, other tasks are also required by these two subroutines. In the maximum rate, subroutine, if fallback is disabled (2:1 block programmed), the atrial refractory period is set equal to the maximum rate interval. On the other hand, the fallback rate programming subroutine must enable the fallback response (i.e., disable 2:1 block) and set the atrial refractory equal to 305 ms.

Magnet Pacing Routine

As shown in FIG. 9B the interrupt service routine initially determines the source of the magnetic field which closed the reed switch. The magnet rate pacing routine is called by placing a permanent magnet over the pacer site. If the programming input port remains active (reed switch closure) for greater than 3.5 ms (seven interrogations) a branch to the magnet pacing routine is executed. This routine provides asynchronous AV sequential pacing (DOO) at the programmed minimum rate and AV delay with 2.0 ms pulsewidths on both channels. The scan cycle through the magnet pacing routine is 14.16 ms as it is in the main pacing routine. This arrangement enables the magnet pacing routine to time the rate and AV delay using the same data stored in the rate routine. The magnet routine also tests to see whether the magnet is present on each scan by sampling the programming input. If the magnet has been removed, the CPU returns to the main pacing routine or the ventricular overdrive pacing routine depending on how it was previously programmed.

Ventricular Overdrive Pacing Routine

The ventricular overdrive pacing routine is executed when the programming pulse decoder decodes 41 pulses. In this mode of operation the atrial sense amplifier is adjusted to a low sensitivity range where it is insensitive to intrinsic cardiac activity so that it can respond exclusively by design to overdrive chest wall stimulation. The triggered output however is on the ventricular channel only. The ventricular rate can be determined externally in this mode within the limits of the programmed minimum rate and maximum rate.

The programming sequence for the overdrive mode automatically programs atrial sensitivity to 7 mv, ventricular sensitivity to off, ventricular output pulse duration to 2 ms and the atrial output pulse duration to "off".

Figure 15:
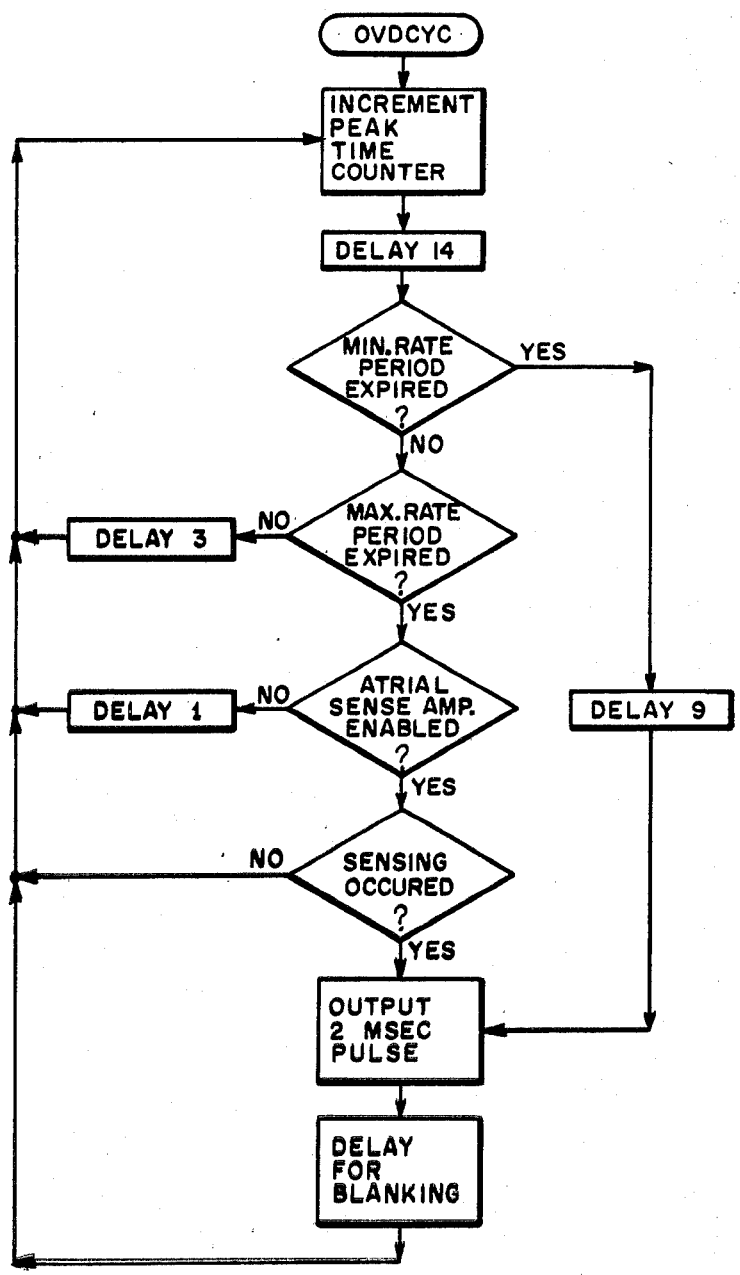
FIG. 15 is a flow chart of the overdrive pacing routine.

The programming sequence for the overdrive mode does not automatically affect the minimum or maximum programmed rate, fallback rate, or AV delay. However, since the overdrive routine as shown in FIG. 15 does not monitor tachycardia, the fallback rate value is not used; nor is the AV delay. The overdrive routine employs the maximum rate interval test as a refractory period. In other words, if the maximum rate interval has not expired according to the RTC register, again using 14.16 scan cycles, the CPU does not proceed to the atrial sense test. Thus the CPU does not see chest wall stimulation until the maximum rate interval has expired. The programmed maximum rate is therefore the software rate limit and the refractory period as shown in FIG. 15. Between the minimum and maximum rates, ventricular pulses of 2.0 duration are synchronized with the overdrive pulses sensed through the atrial sense amplifier.

Exit from the overdrive routine is accomplished only by programming STAT SET. The reason for this is that STAT SET is the only programming sequence which automatically accesses the main pacing routine. Thus as shown in FIG. 9B after the programming decoder routine is finished, the interrupt service routine tests to see whether the overdrive pacing routine or main pacing routine is programmed. If only parameters have been programmed during the interrupt, prior selection of the overdrive mode will continue to be honored.

The above-described cardiac pacer takes advantage of the versatility of microprocessor based pacing systems by employing existing hardware with improved software to enhance the safety and reliability of the overall system, particularly in the tachycardia response mode. The pacer is provided with alternate techniques for handling tachyarrhythmia, namely 2:1 block rendering the CPU insensitive to every other P-wave above a given maximum rate, and programmable fallback mode with progressively declining rate in the VVI mode. By programming 2:1 block automatically during STAT SET the software is able to establish an initial preference for 2:1 block response. This response mode was chosen because fallback is a new and unique way of responding to atrial tachycardia and is not well understood in the industry. Although the atrial sense amplifier is off in the STAT SET mode, (i.e., the pacer is incapable of responding to atrial tachycardia), the STAT SET programming technique is used to initialize all of the parameters, after which individual parameters are set to the values of choice by the physician. Preloading 2:1 block makes it encumbent upon the physician to affirmatively request fallback response mode each time he implants a new pacer in a patient thus diminishing the risk of inadvertantly programming an arrhythmia response mode with which the physician is not adequately familiar or which is inappropriate for a given patient. The fallback routine is improved by strengthening the fallback exit requirements in two ways: resetting the arrhythmia counter to a full count upon the occurrence of a single atrial tachycardia; and lengthening the R to R interval before exiting the fallback routine to shift the phase of the R-waves relative to the P-waves to avoid hiding atrial tachycardias under the blanking period. Both of these steps make it more difficult to exit the fallback routine and are primarily directed at avoiding oscillation in and out of the fallback routine by virtue of intermittently recurring atrial tachycardia.

Blanking techniques are also improved by providing atrial blanking on ventricular sensing and by adjusting both refractory periods and the real time clock to account for the time consumed by such blanking.

The technique for returning from a programming interrupt request is also an improvement. Instead of attempting to return to the point in the main pacing routine at which the interrupt occurred, the improved software directs the CPU to a point in the main pacing routine just after a ventricular event regardless of the point at which the programming interrupt occurred. This novel technique maximizes the time for resynchronization of the pacing pulses with intrinsic heart rhythms and avoids inadvertent competitive stimulation at a dangerous point in the natural cardiac cycle of the patient.

Moreover, all of the foregoing features are achieved in a way which still accommodates programming by preexisting magnetic programmers already in the hands of physicians throughout the world.

Many variations and substitutions may be made in the above described circuitry and software consistent with the fundamental principles of the invention. For example, the system may be modified for bipolar leads or telemetry or specified as an external pacer. While the programmability features are highly desirable and are involved in certain aspects of the invention, it is not essential for all aspects of the invention, particularly with respect to the operation of the main pacing and fallback routines which are automatically interactive. Software functions may also be executed by other types of microprocessors in an analogous fashion, or even by other types of sequential processing systems.

Although the digital circuits are designed for use in a single hybrid circuit, it may be feasible to incorporate most of the circuitry in a custom VLSI chip.

Accordingly, various changes may be made in the above construction and software without departing from the spirit or scope of the invention, and it should be understood that all matter contained in the above description or shown in the accompanying drawings and appendix are to be interpreted as illustrative and not in a limiting sense, the scope of the invention being indicated by the appended claims and all equivalents thereto.

What is claimed is:

1. A cardiac pacer having an atrial tachycardia response mode, comprising
    atrial sense means for producing an output indicative of atrial activity,
    normal pacing logic means for producing stimulation outputs at a predetermined minimum rate including a clock register for keeping time, means for regularly incrementing said clock register, means for resetting said clock register upon the expiration of a minimum rate interval or an atrial sense output, whichever comes first, and means for producing a stimulation output when said clock register attains a predetermined number,
    register means for determining a maximum rate interval,
    register means for determining an atrial refractory period,
    means for inhibiting said atrial sense means output to said resetting means during said atrial refractory period,
    means for monitoring said atrial sense means output during the interval between the end of said atrial refractory period and the end of said maximum rate interval for producing an arrhythmia signal,
    means responsive to said arrhythmia signal for altering the mode of operation of said normal pacing logic means so as to disassociate the ventricles from the atria, and
    2:1 block means for setting said atrial refractory period equal to said maximum rate interval,
    whereby every other atrial sense means output exceeding the maximum rate is inhibited and said arrhythmia signal is disabled.

2. The pacer of claim 1, wherein said maximum rate interval register means is externally programmable.

3. The pacer of claim 2, wherein said atrial refractory period is nominally fixed when not set equal to said maximum rate interval.

4. The pacer of claim 1, further comprising
    means defining a plurality of standard parameter values, said normal pacing logic means being responsive to said parameter values for determining the pacing conditions, and means responsive to an external programming signal for automatically adopting said standard values and for enabling said 2:1 block means.

5. The pacer of claim 4, further comprising means responsive to externally generated programming signals for disabling said 2:1 block means, whereby said atrial refractory period is restored to its fixed value different from said maximum rate interval period.

6. A computer-based cardiac pacer having programming interrupt request means, comprising at least one pacer terminal, sense means connected to said terminal for sensing cardiac activity and issuing a respective output signal, computer means including digital storage means having stored program means for defining a series of instructions and processing means for fetching and executing said instructions sequentially having an interrupt request input, said stored program means including means defining a pacing routine including means for interrogating said sense means output and decision means for producing a stimulation signal, means responsive to said stimulation signal for applying a stimulation output to said terminal, interrupt means responsive to an external signal for applying a programming signal to said interrupt request input, said stored program means including means defining an interrupt service routine for decoding said programming signal and storing parameter values indicated thereby, said processing means having further means responsive to an interrupt request input at any time for substituting said interrupt service routine for said pacing routine, said interrupt service routine further including means for returning to a predetermined point in said pacing routine in a condition corresponding to a time immediately following a ventricular event, whereby the pacing routine is reentered following the servicing of a programming interrupt request at a point allowing maximum time to respond to intrinsic cardiac activity regardless of the point at which the main pacing routine was interrupted by the programming signal.

7. A cardiac pacer having an arrhythmia response mode, comprising atrial sense means for producing a respective output, normal pacing logic means for producing stimulation outputs at a predetermined minimum rate, first arrhythmia detection means responsive to atrial tachycardia for issuing an arrhythmia signal, means responsive to said arrhythmia signal for causing aid pacer to enter an arrhythmia response mode by altering the mode of operation of said normal pacing logic means so as to disassociate the ventricles from the atria by stimulating the ventricles at a rate independent of the atria, second arrhythmia detection means for monitoring atrial tachycardia during said arrhythmia response mode for producing a return signal, means responsive to said return signal for causing the pacer to exit said arrhythmia response mode and to resume the normal mode of operation of said pacing logic means, and means for shifting the phase of said ventricular stimulation at a predetermined point in said arrhythmia response mode.

8. The pacer of claim 7, wherein said second arrhythmia means includes an arrhythmia register, means for incrementing said arrhythmia register during the arrhythmia response mode by a first predetermined number upon each atrial sense means output within a maximum rate interval from the preceding atrial sense means output, means for decrementing said arrhythmia register by a second predetermined number during said arrhythmia response mode upon the occurrence of each ventricular event, means for issuing said return signal when said arrhythmia register is reduced to a third predetermined number, and means responsive to said arrhythmia register attaining a fourth predetermined number higher than said third predetermined number for enabling said phase shifting means.

9. The pacer of claim 8, wherein said phase shifting means includes means for lengthening the R to R interval between ventricular stimulation pulses by a predetermined amount during said arrhythmia response mode.

10. The pacer of claim 9, further comprising means for blanking said atrial sense means output for a predetermined blanking interval during the arrhythmia response mode whenever a ventricular stimulation output is produced, said phase shifting means including means for lengthening the R to R interval defining the ventricular stimulation period during the arrhythmia response mode by an amount sufficient to extend the interval beyond the end of the atrial blanking interval which would have occurred had the R to R interval not been changed.

11. A cardiac pacer having an arrhythmia response mode, comprising artial sense means for producing a respective output, normal pacing logic means for producing stimulation outputs at a predetermined minimum rate having a normal mode of operation and an arrhythmia response mode of operation, first arrhythmia detection means operative during said normal mode for monitoring atrial tachycardia including an arrhythmia register, means for incrementing said arrhythmia register by a first predetermined number upon the occurrence of an atrial sense means output within a maximum rate interval following the preceeding atrial sense means output, means for decrementing said arrhythmia register upon each occurrence of a ventricular event, and means for issuing an arrhythmia signal when said arrhythmia counter attains a third predetermined number means responsive to said arrhythmia signal for causing the pacer to enter said arrhythmia response mode by altering the mode of operation of said pacing logic means so as to disassociate the ventricles from the atria by stimulating the ventricles at a rate independent of the atria, second arrhythmia detection means operative during said arrhythmia response mode for monitoring atrial tachycardia including an arrhythmia register, means for incrementing said arrhythmia register by a fourth predetermined number upon the occurrence of an atrial sense means output within said maximum rate interval, means for decrementing said arrhythmia register by a fifth predetermined number upon the occurence of a ventricular event and means for issuing a return signal when the count in said arrhythmia register is reduced to a sixth predetermined number, the ratio of said fourth and fifth predetermined numbers being different from the ratio of said first and second predetermined numbers, means responsive to said return signal for causing the pacer to resume the normal operation mode of said pacing logic means.

12. The pacer of the claim 11, wherein said third and fourth predetermined numbers are equivalent and said second and fifth predetermined numbers are equivalent.

13. A cardiac pacer having an arrhythmia response mode, comprising atrial sense means for producing a respective output, multi-mode pacing logic means having a normal mode and an arrhythmia response mode for producing stimulation outputs at a predetermined rate, first arrhythmia detection means for issuing an arrhythmia signal when atrial tachycardia activity exceeds an entry threshold, means responsive to said arrhythmia signal for causing the pacer to enter said arrhythmia response mode by altering the mode of operation of said pacing logic means to effectively disassociate the ventricles from the atria by stimulating the ventricles at a rate independent of the atria, second arrhythmia detection means operative during an arrhythmia response mode for issuing a return signal when atrial tachycardia activity falls short of an exit threshold, means responsive to said return signal for causing the pacer to restore the pacing logic means to the normal mode of operation, said thresholds being determined such that the level of atrial tachycardia activity required to remain in the arrhythmia mode is less than that required to enter the arrhythmia mode, whereby an entry/exit hysteresis is established to avoid oscillation between the normal mode and arrhythmia response mode during intermittently recurring atrial tachycardia.

* * * * *